US012414690B2

(12) United States Patent
D'Ippolito

(10) Patent No.: US 12,414,690 B2
(45) Date of Patent: Sep. 16, 2025

(54) CUSTOMIZED ABLATION TO CORRECT VISUAL AMETROPIA

(71) Applicant: IVIS TECHNOLOGIES S.r.l., Taranto (IT)

(72) Inventor: Giuseppe D'Ippolito, Taranto (IT)

(73) Assignee: IVIS TECHNOLOGIES S.r.l., Taranto (IT)

( * ) Notice: Subject to any disclaimer, the term of this patent is extended or adjusted under 35 U.S.C. 154(b) by 627 days.

(21) Appl. No.: 17/541,597

(22) Filed: Dec. 3, 2021

(65) Prior Publication Data

US 2022/0175243 A1   Jun. 9, 2022

(30) Foreign Application Priority Data

Dec. 4, 2020   (EP) ..................................... 20212011

(51) Int. Cl.
*G02C 7/04* (2006.01)
*A61B 3/00* (2006.01)
(Continued)

(52) U.S. Cl.
CPC ............ *A61B 3/107* (2013.01); *A61B 3/1005* (2013.01); *A61B 3/102* (2013.01); *A61B 3/103* (2013.01); *G16H 40/63* (2018.01)

(58) Field of Classification Search
CPC ........... A61B 3/103; A61B 3/14; A61B 3/152; A61B 3/113; A61B 3/1225; A61B 3/024;
(Continued)

(56) References Cited

U.S. PATENT DOCUMENTS 6,241,356 B1   6/2001   Von Wallfeld et al.
11,883,328 B2 *   1/2024   Riedel .................. A61F 9/00804
(Continued)

FOREIGN PATENT DOCUMENTS

EP          1459676 A1    9/2004
JP       2002 345755 A   12/2002
(Continued)

OTHER PUBLICATIONS

Extended European Search Report issued for corresponding EP Application No. 20212011.9, mailed Jul. 16, 2021.
(Continued)

*Primary Examiner* — Dawayne Pinkney
(74) *Attorney, Agent, or Firm* — Renner, Otto, Boisselle & Sklar, LLP

(57) ABSTRACT

The present invention relates to apparatuses, computer programs, and methods for visual ametropia correction. In a first example, a position of a desired focusing point relative to a retina of an individual eye may be determined, based on obtained topographic information of the anterior surface and of the posterior surface of the cornea, and refractive aberration information for the eye. In a second example, correction information relating to the anterior surface of the cornea may be determined, such as to optimize focusing onto a retina of the eye, based on the obtained topographic information of the anterior surface and of the posterior surface of the cornea and based on obtained topographic information of an anterior surface and of a posterior surface of a lens of the individual eye.

14 Claims, 14 Drawing Sheets

Figure 1A:
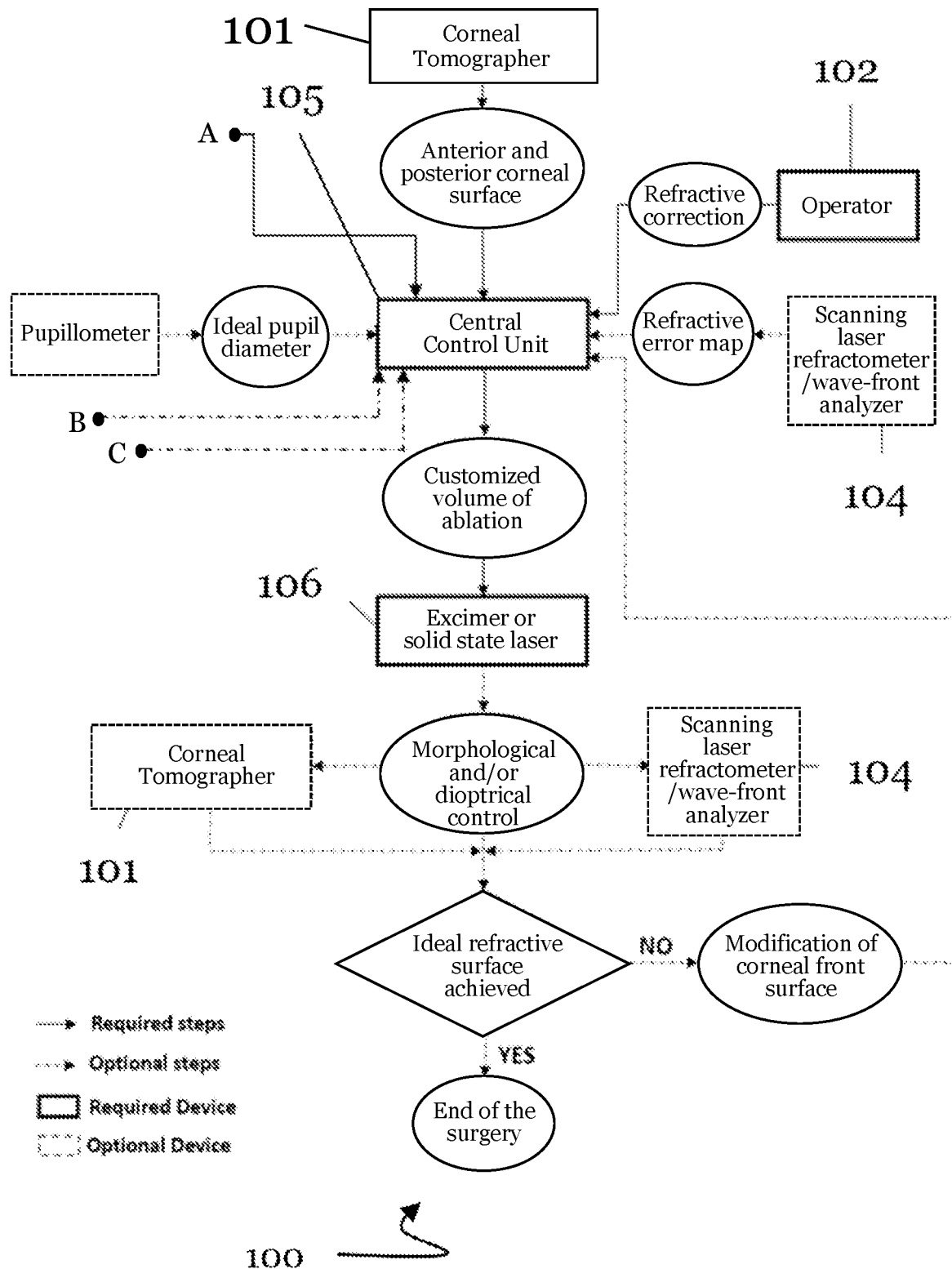
Figure 1B:
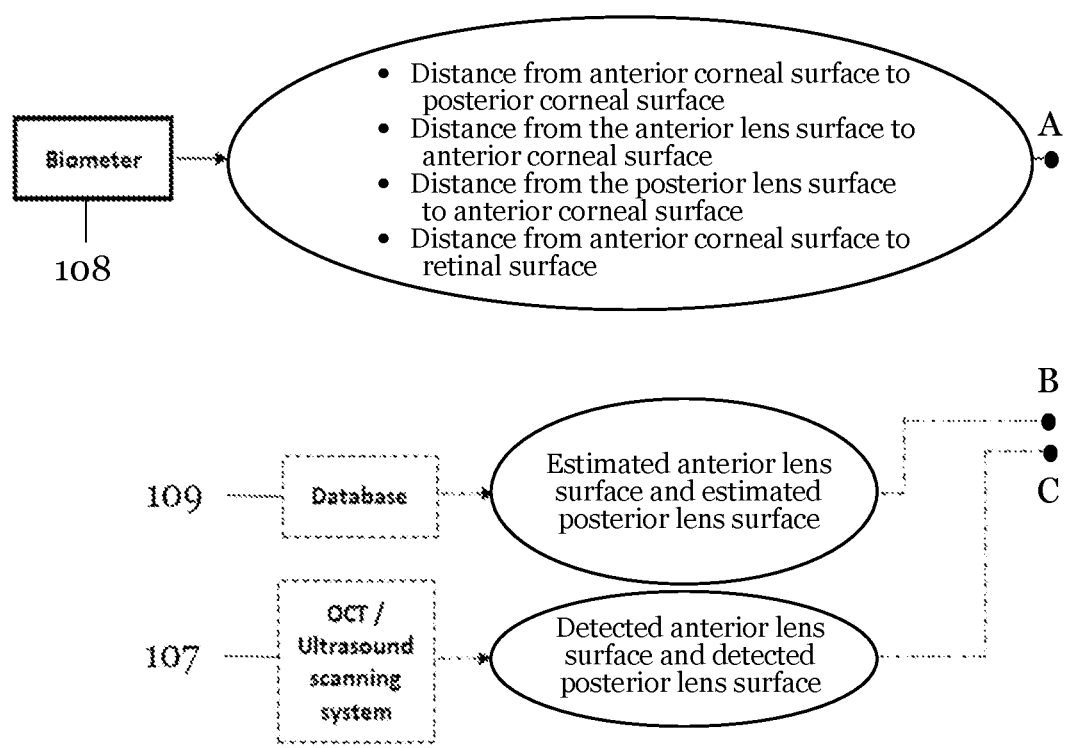

(51) Int. Cl.
*A61B 3/02* (2006.01)
*A61B 3/10* (2006.01)
*A61B 3/103* (2006.01)
*A61B 3/107* (2006.01)
*A61B 3/12* (2006.01)
*A61F 9/02* (2006.01)
*G16H 40/63* (2018.01)

(58) Field of Classification Search
CPC ......... A61B 3/032; A61B 3/18; A61B 3/1015; G09G 2340/0492; G02C 5/00; G02C 7/04
USPC ........... 351/159.02, 200, 205–206, 208–211, 351/221–223, 245–246, 41
See application file for complete search history.

(56) References Cited

U.S. PATENT DOCUMENTS

| | | |
|---|---|---|
| 2012/0044454 A1 | 2/2012 | Canovas Vidal et al. |
| 2015/0131054 A1 | 5/2015 | Wuellner et al. |
| 2015/0250585 A1* | 9/2015 | Rosen .................... A61F 2/1613 623/6.26 |
| 2017/0095147 A1* | 4/2017 | Copland ................ A61B 3/107 |
| 2017/0189233 A1* | 7/2017 | Dewey ................... A61B 3/103 |

FOREIGN PATENT DOCUMENTS

| | | |
|---|---|---|
| WO | 98/42291 A2 | 10/1998 |
| WO | 01/28410 A1 | 4/2001 |
| WO | 2010/035139 A2 | 4/2010 |
| WO | 2016/126331 A1 | 8/2016 |
| WO | 2019/202104 A1 | 10/2019 |
| WO | 2020/095289 A1 | 5/2020 |

OTHER PUBLICATIONS

Partial European Search Report issued for corresponding EP Application No. 20212011.9, mailed May 17, 2021.

* cited by examiner

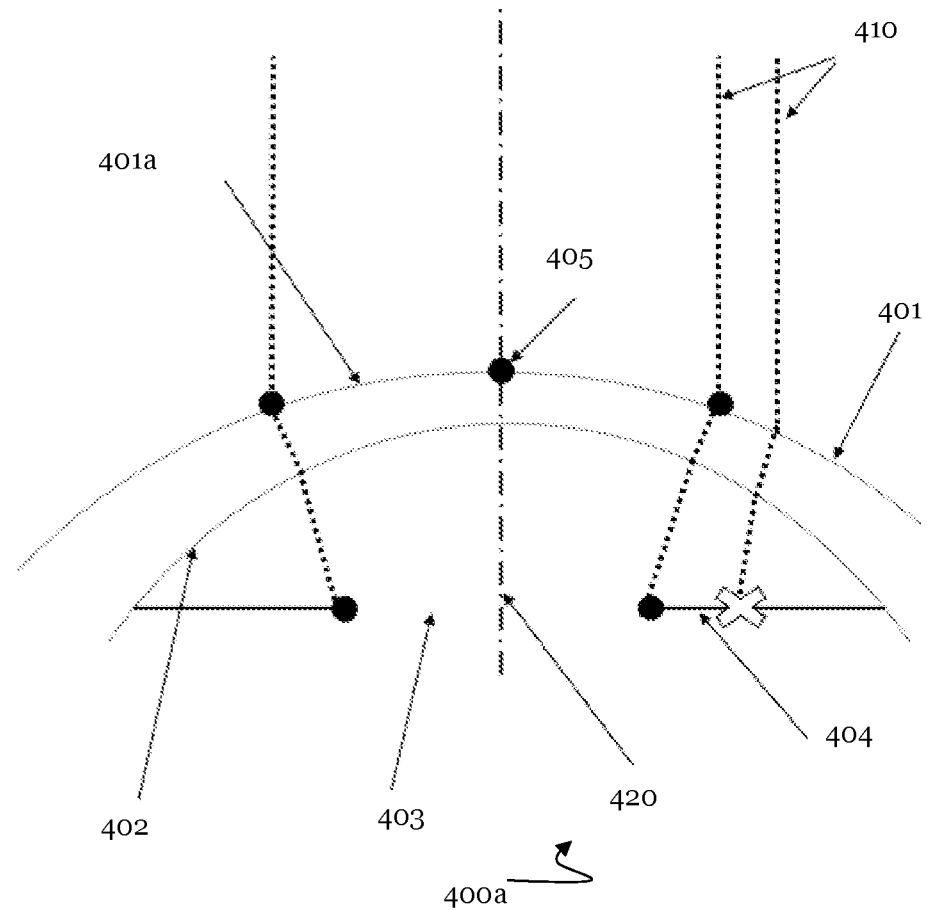

CUSTOMIZED ABLATION TO CORRECT VISUAL AMETROPIA

This application claims priority of European Patent Application No. 20212011.9, filed Dec. 4, 2020, the entire disclosure of which is hereby incorporated by reference.

1. TECHNICAL FIELD

The present invention relates to customized ablation to correct visual ametropia, and in particular to determining a customized volume of corneal tissue to be ablated, corresponding apparatuses and computer programs.

2. DESCRIPTION OF THE PRIOR ART

Corneal refractive surgery has significantly evolved over the last twenty years leading to customized ablation, wherein ablation profiles are adapted to the specific needs of individual patients to correct their visual ametropia.

In treating the cornea of an eye to correct visual ametropia, usually a refractive error is first determined (e.g., refractive aberration information). In the prior art, a volume of tissue equivalent to the lens needed to correct the refractive aberration information, is then calculated, using the corneal index of refraction, to correct the patient's vision, and the cornea is treated by means of a laser to ablate the calculated lens that corrects the visual ametropia.

In a more recent prior art, several different methods were introduced for determining the target profile of the anterior corneal surface instead of calculating the volume of tissue equivalent to the lens needed to correct the refractive aberration information. In an example, the target profile of the anterior corneal surface may be subjectively determined by the treating doctor, i.e., the treating doctor may determine the target profile such that it fulfills clinical requirements based on the doctor's clinical experience. WO 98/42291 relates to such an approach. Based on an available resolution, a set of points on the cornea of the eye is determined together with a position of each point. A computer then determines, for each point out of the determined set of points, a distance between the actual surface of the cornea and a predetermined reference surface. The predetermined reference surface may be determined based on clinical experience and/or alternative methods. The determined distances then define the profile for corneal tissue ablation.

In another example, diopter correction values may be determined for various points on the cornea of the patient. These diopter correction values may be determined by searching diopter values which optimize a focalization at foveal level of a light ray impinging on the cornea as generated by a light source arranged at infinite distance (EP 1 352 623). The set of diopter correction values then defines the profile for corneal tissue ablation.

Further prior art can be found in US 2015/131054 A1 and WO 2019/202104 A1.

However, the known methods take into account the structure of the individual eye only to a limited extent. Correspondingly, the current methods to determine the target profile of the cornea are not always optimal in terms of improvement of the quality of vision. Even more so, the current methods may lead to an ablation of an amount of corneal tissue which may be (significantly) higher than required.

Therefore, there is a need for improving the determination of the target profile of the cornea such that corneal tissue ablation may be minimized and/or such that the quality of vision is further enhanced.

3. SUMMARY OF THE INVENTION

According to an aspect, the above need is at least partly met by apparatuses according to claims 1 and 7, and by corresponding computer programs and corresponding methods according to claims 11 to 14.

A first embodiment of the present invention relates to an apparatus for visual ametropia correction. The apparatus comprises means for obtaining topographic information of an anterior surface and topographic information of a posterior surface of a cornea of an individual eye. The apparatus further comprises means for obtaining distance information of a retina of the eye relative to the anterior surface of the cornea of the individual eye. The apparatus also comprises means for determining a position of a desired focusing point relative to the retina, based on the topographic information of the anterior surface and of the posterior surface of the cornea, and refractive aberration information for the eye.

An underlying idea of the present invention is that a major limitation of prior art approaches is caused by the fact that these take into account the individual structure of the eye to a limited extent. A correction of visual ametropia based on data for which individual eye information is only considered in a limited way is therefore not optimal. However, obtaining more individual eye data requires that this data is reliably obtained which, in the prior art is not always the case.

According to the present embodiment, a desired focusing point is determined, i.e. a point on which the eye should focus to optimize vision, based on refractive aberration information for the individual eye (e.g., measured information, e.g. in a vision test conducted by an ophthalmologist or in a wavefront analyzer or in a scanning laser refractometer measurement) and taking into account topographic information relating to the anterior and posterior surfaces of the cornea of the individual eye (e.g., measured information). In a subsequent step, this desired focusing point may then be used to determine the required modifications to the anterior corneal surface such as to optimize vision for the individual eye.

Especially dealing with complex cases, as irregular astigmatism or ectasia, the posterior corneal surface of the eye may have relevant irregularities. A correction that is calculated solely based on the anterior corneal surface may not be satisfactory, since the (neglected) irregular posterior corneal shape may cause not compensated refractive aberrations despite the applied correction. Correcting visual ametropia solely based on topographic information of the anterior corneal surface may therefore not be optimal. Since in the real eye, refraction occurs not only at the anterior corneal surface but also at the posterior corneal surface (due to a transition from the denser corneal stroma of the eye to the less dense aqueous humour of the eye), taking into account the specific patient's posterior corneal surface (e.g., including distance information of the posterior corneal surface relative to the anterior corneal surface) may allow a better determination of the correction information. This is particularly the case, since posterior corneal surfaces may strongly vary from patient to patient, and may have irregular shapes (which may in general be described not only by linear or quadratic functions, but also by higher order functions, e.g., functions of third order and above, e.g. polynomials that may not have a shape that could be approximated by a sphere or an ellipse, etc.).

However, the inventor of the present invention has realized that refractive error information as well as topographic information of the corneal surfaces may not always be perfectly accurate and/or the individual patient may have e.g. an irregularly shaped lens such that the above steps for determining a desired focusing point do not always lead to an accurate determination of the desired focusing point. It is indeed crucial that the contribution of e.g. the posterior corneal surface of the individual patient is reliably obtained, just as the refractive aberration information.

Means for obtaining distance information of the retina of the eye relative to the anterior surface of the cornea of the individual eye and determining the position of the desired focusing point relative to the retina, according to the present embodiment, therefore allows the provision of a reliability measure. Thereby, more accurate data about the individual eye may be required for the use for visual ametropia correction. By determining a reliability measure (e.g., the distance of the desired focusing point relative to the retina) based on topographic information of both the anterior and posterior corneal surface and refractive aberration information allows a verification whether the obtained data is reliable or not.

Topographic information of a surface of the cornea (e.g., anterior and/or posterior surface) may include a profile (e.g., a plurality of coordinates defining one or more actual points on the surface of the cornea, a plurality of points approximating the surface of the cornea, or a function fitted to the surface of the cornea, etc.). The topographic information may for example be provided in the form of a number of points in an x-y-z coordinate system. Of course, other coordinate systems may be used. The correction information may then be determined based on the topographic information of the anterior and posterior corneal surfaces as well as the desired focusing point.

It is noted that the apparatus described above may not necessarily include means for determining or calculating the topographic information and/or the desired focusing point. The means for obtaining may be implemented by means for receiving the respective information from other devices or an operator of the apparatus. In such examples, the apparatus may use the received information directly for determining the correction information and/or the desired focusing point, and/or it may further process the received information. For example, the topographic information and/or the desired focusing point relating to a patient may be retrieved from a memory, a database, a server in a cloud, and/or from corresponding diagnostic devices, or these may simply be input by an operator of the apparatus, e.g., a surgeon.

The refractive aberration information may comprise subjective refraction for the eye (such as one or more spherical diopter values, and/or one or more cylindrical diopter values and one or more cylinder axes, for example), e.g. as obtainable by a typical vision test. Thus, in some examples, the refractive aberration information comprises or consists of subjective refraction. Additionally or alternatively, the apparatus may comprise means for obtaining refractive aberration information for the eye from a scanning laser refractometer (e.g. as disclosed by EP 1 459 676) and/or a wavefront analyzer or a similar device. For example, the refractive aberration information may comprise one or more parameters, e.g. polynomial coefficients, obtainable from a wave-front analyzer. The scanning laser refractometer and/or the wave-front analyzer may for example be adapted to provide the refractive aberration information in the form of a map of refractive errors, e.g., for selected regions on the anterior surface of the cornea, as explained. For example, the refractive errors may be expressed as diopter values, coefficients for one or more polynomials, such as Zernike polynomials, etc. The apparatus may include a scanning laser refractometer and/or wave-front analyzer or simply may import, by means of any media, the refractive aberration information from a laser refractometer and/or a wave-front analyzer. The refractive aberration information may also be obtained, e.g., by an operator of the apparatus which may input this information, e.g., via an interface. Additionally or alternatively, the refractive aberration information may be obtained from a storage medium.

In some examples, the means for determining a position of the desired focusing point may be further adapted to determine the position based on a lens model estimating the lens of the eye (e.g. a statistical lens model that may, e.g., describe average lens parameters based on data measured for a multitude of eyes). Thus, also the (estimated) contribution of the lens to the refraction within the eye may be taken into account when determining the desired focusing point. By determining the desired focusing point relative to the retina, as described, the reliability of the lens model and/or of the refractive aberration information can be analyzed. It can be verified whether the desired focusing point is indeed located on or close to the retina, based on distance information as measured for the individual eye. For example, if the distance of the desired focusing point relative to the (measured) retina (i.e. the reliability measure) is above a threshold, for example above 500 µm, more preferably above 300 µm, most preferably above 100 µm, the data available of the individual eye (e.g. the refractive aberration information and/or the lens model estimating the lens of the eye), may be determined to be erroneous.

If the deviation is too big, e.g. larger than the thresholds described above, it may e.g. be determined that the patient has a lens that does not conform to the lens model (and/or that the refractive aberration information and/or the topographic information relating to the anterior and/or posterior cornea surfaces is inaccurate).

The lens model of the eye may for example comprise a lens profile (e.g. an anterior and/or a posterior lens profile). The lens profile may comprise a plurality of coordinates defining one or more actual points on an anterior and/or posterior surface of the lens, a plurality of points approximating the anterior and/or posterior surface of the lens, or a function fitted to the anterior and/or posterior surface of the lens, similarly as described above with respect to topographic information of a surface of the cornea. The lens profile may additionally of alternatively comprise distance information, e.g. a distance of the anterior and/or posterior surface of the lens model relative to the anterior surface of the cornea (e.g. a statistical distance information, that may, e.g., describe an average distance of the anterior and/or posterior surface of the lens model from an anterior surface of the cornea based on data measured for a multitude of eyes).

In some examples, the parameters of the lens model may be adapted to the individual eye. For example, the parameters may be scaled based on the distance information of the retina relative to the anterior surface of the cornea. The parameters of the lens model may, however, not include any measured parameters. Additionally or alternatively, they may or may not be obtained using wavefront measurements and/or using a fitting to wavefront measurements.

In some examples, the apparatus may further comprise means for obtaining distance information. The distance information may comprise a distance of an anterior surface of a lens of the eye relative to the anterior surface of the cornea of the individual eye, and/or a distance of a posterior surface of the lens relative to the anterior surface of the cornea of the individual eye (e.g. information measured for the individual eye). The obtained distance information may be used to place the lens model, which models the lens of the eye (e.g. by an anterior and/or posterior lens surface), according to the distance information. Thereby, the reliability measure, i.e., the distance of the desired focusing point relative to the retina may even be further refined allowing a more accurate determination whether the available individual eye data is accurate. This in turn allows a more individualized visual ametropia correction when the available individual eye data is used for visual ametropia correction.

In some examples, the means for determining the position of the desired focusing point relative to the retina may be further adapted to base the determining on a lens profile of the lens model modeling the lens of the eye. Thereby, for determining the distance of the desired focusing point relative to the retina not only topographic information of the anterior and the posterior corneal surface is taken into account, but also a model of the lens profile of the lens of the eye. Thereby, an even more refined reliability measure is obtained leading to even more reliable results, e.g., of whether the obtained individual eye data is accurate.

In some examples, the apparatus may be adapted to issue a warning if the position of the desired focusing point relative to the retina exceeds a predetermined threshold. Thereby, an operator of the apparatus is warned that the available data may be erroneous, and the available data may be reconsidered before this data is used to correct visual ametropia.

In some examples, the means for obtaining the desired focusing point may be further adapted to determine the desired focusing point by ray tracing of at least one light ray refracted according to the topographic information of the anterior surface and of the posterior surface of the cornea (possibly including distance information of the posterior surface relative to the anterior surface), and according to optical means that correspond to a correction of the refractive aberration information for the eye. As known to the skilled person, refraction at an interface between two materials (e.g., air and corneal tissue, corneal tissue and the aqueous humour, aqueous humour and lens, lens and vitreous humour, etc.) may be calculated, e.g., based on Snell's law and the refractive indices of the materials. Thus, based on the topographic information (e.g. a profile) of the corneal surface(s) (possibly including distance information), and the refractive indices of the relevant materials (known to the skilled person), the refraction for light rays passing through the anterior and posterior surfaces of the cornea and possible also the anterior and posterior surfaces of the lens may be calculated.

Using the ray-tracing mentioned in the preceding paragraph, the available eye data may be verified by tracing one or more light rays. The light rays may impinge on optical means that correspond to a correction of the refractive aberration information for the eye (e.g., a lens that corresponds to a correction of the refractive aberration information) in a manner parallel to an optical axis of the eye. The light rays are refracted by the optical means, the anterior and posterior corneal surfaces and possibly also the lens model (possibly as placed according to the distance information and possibly also as described by profiles for anterior and/or posterior surfaces) before the light rays intersect with the optical axis within the eye. The intersection(s) of the light ray(s) with the optical axis within the eye (e.g. their center of gravity) may define the desired focusing point from which the relative distance to the retina can be determined.

In some examples, a region within a certain radius around a corneal apex (or a center of the anterior corneal surface) may be considered for ray-tracing. For example, a region on the anterior surface which is within a diameter corresponding to the diameter of the pupil of the eye, detected according to a predefined light environment, preferably, but not necessarily, obtained by a pupillometer, may be considered. For a regular or randomized grid of points within such a region, ray-tracing may then be performed, such that for each point, a position of the desired focusing point relative to the retina may be obtained, as described in the previous paragraph. By using an appropriate number of points, an estimate of the desired focusing point relative to the retina may be obtained by, e.g., calculating the center-of-mass or taking a weighted average of the determined positions.

In some examples, the ray-tracing relates to at least one first light ray impinging on the optical means in a manner parallel to an optical axis of the eye (forward ray-tracing). For example, forward ray-tracing may be performed for a plurality of first light rays, each first light ray impinging on a respective point of a grid of points within a selected region of the anterior surface of the cornea, as outlined in the preceding paragraphs.

In the case of forward ray-tracing, the position of the desired focusing point relative to the retina may be defined as an intersection of the at least one first light ray with the optical axis of the eye, after being refracted by the optical means, the anterior and posterior surfaces of the cornea and possibly also the lens model (possibly as placed according to the distance information and possibly also as described by profiles for anterior and/or posterior surfaces). By doing this determination for several light rays, wherein each light ray impinges on a point of a grid of points on the anterior surface, the desired focusing point can be obtained by taking, e.g., the weighted average of the relative distances between the intersections of the light rays with the optical axis and the retina. Thereby, a reliable estimate of the desired focusing point can be determined.

In some examples, additionally or alternatively to forward ray-tracing, the ray-tracing may relate to at least one second light ray emerging from the desired focusing point (reverse ray-tracing). For example, reverse ray-tracing may be performed for a plurality of second light rays, each second light ray exiting optical means that correspond to a correction of the refractive aberration information for the eye (e.g., a lens that corresponds to a correction of the refractive aberration information) after being refracted by the optical means, the posterior and anterior surfaces of the cornea and possibly also the lens model (as placed according to the distance information and possibly also described by profiles for anterior and posterior surfaces).

In the case of reverse ray-tracing, the desired focusing point may be determined (e.g., iteratively) at least in part such as to minimize an angle between an optical axis of the eye and the at least one second light ray as it exits the optical means, after being refracted by the lens model (as placed according to the distance information and possibly also described by profiles for anterior and posterior surfaces), the posterior and anterior corneal surfaces (as determined by the respective topographic information), and the optical means (e.g., mimicking a lens that corresponds to a correction of the refractive aberration information). For example, the desired focusing point may be determined such that the angle between the ray-traced light ray exiting the optical means and the optical axis is essentially zero. Similarly as described above, this may be performed for a set of points on the anterior corneal surface.

In some examples, the apparatus may further comprise means for determining correction information relating to the anterior surface of the cornea, such as to optimize focusing onto the desired focusing point, based on the topographic information of the anterior surface and of the posterior surface of the cornea. In some examples, the focusing may also be optimized based on distance information between anterior and posterior surfaces of the cornea, and/or the lens model, and/or distance information for the lens model.

The correction information may comprise a correction that needs to be applied to the anterior corneal surface, e.g., such that light rays refracted by the corrected anterior corneal surface and by the posterior surface are optimally focused onto the desired focusing point. The correction information may define a correction in the form of an ablation volume, an ablation profile and/or a target profile and/or a target slope of the anterior corneal surface, for example. The correction information may include values relating to individual points on the anterior surface of the cornea, e.g., a grid of points on the anterior surface of the cornea. The correction information may then be used to ablate a corresponding corneal volume.

In some examples, the correction information may comprise a target slope and/or a target profile of the anterior surface of the cornea. For example, the correction information may relate to one or more points (e.g., forming a grid) on the anterior surface of the cornea, wherein for each point a target slope or target thickness may be indicated, e.g. in form of a map or a profile of the target anterior corneal surface. The correction information may however also relate to values that are to be ablated, e.g. a target ablation volume and/or a target ablation thickness (for each point). Target ablation values may be obtained by intersecting the topographic information of the anterior corneal surface and, e.g., a target profile for the anterior corneal surface that optimizes vision.

Using the ray-tracing mentioned in the preceding paragraphs, the correction information may be determined at least in part such as to optimize focusing on the desired focusing point. In other words, the correction that needs to be applied to a certain point on the anterior surface of the cornea is determined, such that the light ray passing through that point is optimally focused onto the desired focusing point, as calculated based on the (corrected) anterior surface topography and based on the topographic information of the posterior surface of the cornea and possibly based on distance information between anterior and posterior surfaces of the cornea, and/or the lens model, and/or distance information for the lens model.

In some examples, similarly as described above, a region within a certain radius around a corneal apex (or a center of the anterior corneal surface) may be considered for ray-tracing. For example, a region on the anterior surface which is within a diameter corresponding to the diameter of the pupil of the eye, detected according to a predefined light environment, preferably, but not necessarily, obtained by a pupillometer, may be considered, similarly as described above. For a regular or randomized grid of points within such a region, ray-tracing may then be performed, such that for each point, the corresponding correction information may be obtained, e.g. the target slope of the anterior surface at that point. By using an appropriate number of points, correction information may be determined in the form of a map of the anterior corneal surface.

In some examples, the ray-tracing relates to forward ray-tracing where at least one first light ray impinges on the anterior surface of the cornea in a manner parallel to an optical axis of the eye. Forward ray-tracing may be performed for a plurality of first light rays, each first light ray impinging on a respective point of a grid of points within a selected region of the anterior surface of the cornea, as outlined above.

In the case of forward ray-tracing, the correction information relating to the anterior surface of the cornea may be determined at least in part such as to optimize focusing on the desired focusing point, i.e. bring the point(s) onto which the ray(s) are focused as closely as possible to the desired focusing point. The point on which a ray is focused may be defined as an intersection of the ray with an optical axis of the eye, after being refracted by the anterior and posterior surfaces of the cornea (possibly under consideration of distance information between anterior and posterior surfaces of the cornea) and possibly also the lens model (possibly as placed according to the distance information and possibly also described by profiles for anterior and posterior surfaces). For example, a target slope of the anterior corneal surface may be determined, such that a distance between the desired focusing point and the mentioned intersection is essentially zero. By doing this determination for several light rays, wherein each light ray impinges on a point of a grid of points on the anterior surface, the necessary correction information to be applied at that point may be determined, such that each light ray impinging on the respective point is optimally focused onto the desired focusing point. Thus, correction information, e.g. a target slope, for the entire grid of points may be obtained. A target profile of the anterior corneal surface may then be determined, e.g. by integrating the determined target slopes.

In some examples, additionally or alternatively to forward ray-tracing, the ray-tracing may relate to at least one second light ray emerging from the desired focusing point (reverse ray-tracing), as described above. Similarly as described above, reverse ray-tracing may be performed for a plurality of second light rays, each second light ray exiting the cornea on a respective point on a grid of points within a selected region of the anterior surface of the cornea, after being refracted by the posterior and anterior surfaces of the cornea (possibly under consideration of distance information between anterior and posterior surfaces of the cornea) and possibly also the lens model (possibly as placed according to the distance information and possibly also described by profiles for anterior and posterior surfaces).

In the case of reverse ray-tracing, the correction information relating to the anterior surface of the cornea may be determined at least in part such as to minimize an angle between an optical axis of the eye and the at least one second light ray as it exits the cornea, after being refracted by the lens model (possibly as placed according to the distance information and possibly also described by profiles for anterior and posterior surfaces) and posterior and anterior corneal surfaces (as determined by the respective topographic information) and possibly under consideration of distance information between anterior and posterior surfaces of the cornea. For example, the correction information may be determined such that the angle between the ray-traced light ray exiting the cornea and the optical axis is essentially zero. Also in this manner, for a grid of points on the anterior surface of the cornea, the necessary correction information may be determined, such that, for each single point of the grid, the angle between the ray-traced light ray exiting the cornea and the optical axis is essentially zero.

Another (second) embodiment of the present invention relates to an apparatus for visual ametropia correction. This apparatus comprises means for obtaining topographic information of an anterior surface and topographic information of a posterior surface of a cornea of an individual eye, means for obtaining topographic information of an anterior surface and/or topographic information of a posterior surface of a lens of the individual eye, and means for obtaining distance information of a retina of the eye relative to the anterior surface of the cornea of the individual eye. The apparatus also comprises means for determining correction information relating to the anterior surface of the cornea, such as to optimize focusing onto the retina of the eye, based on the topographic information of the anterior surface and of the posterior surface of the cornea and the topographic information of the anterior surface and of the posterior surface of the lens.

It is noted that the first and second embodiments, and all aspects described herein pertaining to these embodiments, may be combined. For example, a single apparatus may be provided implementing both embodiments. Unless expressly outlined to the contrary, aspects described with reference to the first embodiment also apply to the second, and vice versa.

Taking into account the topographic information of the anterior and the posterior surface of the lens of the individual eye—and not only the anterior and posterior corneal surface of the individual eye—in the determination of the correction information allows obtaining an ablation volume which better fits the needs of the individual patient and improves vision correction, since the refractive contribution of the lens may be taken into account.

As already outlined above, an underlying idea of the present invention is that a major limitation of prior art approaches is that the individual structure of the eye is only taken into account to a limited extent. The prior art approaches neglect the refractive contribution of the lens of the eye or it may be considered only in a very limited extent. For example, in case of an abnormal shape of the lens, a correction that is calculated solely based on surface information of the cornea and/or a regular shape of the general lens model may not be satisfactory, since the (neglected) abnormal shape of the individual lens may lead to refractive aberrations despite the applied correction. The correction is therefore not optimal. Taking into account the specific patient's shape of both the cornea and the lens allows a better determination of the correction information. Thus, the vision correction of the individual patient may be improved. This is particularly the case, since both the corneal surfaces and the lens surfaces may strongly vary from patient to patient, and may have irregular shapes (which may in general be described not only by linear or quadratic functions, but also by higher order functions, e.g., functions of third order and above, e.g. polynomials that may not have a shape that could be approximated by a sphere or an ellipse, etc.). Considering the specific topography (morphology or shape) of the cornea and of the lens of the eye when determining the correction information that optimizes focusing onto the retina of the eye, allows eliminating this issue. Taking into account the refractive contribution of not only the corneal surfaces but also the refractive contribution of the lens of the individual patient allows optimizing the correction and often minimizing the ablation volume necessary for the correction.

Similarly as already described above, the apparatus may not necessarily include means for determining or calculating the topographic information and/or the distance information of the retina of the eye. The means for obtaining may be implemented by means for receiving the respective information from other devices or an operator of the apparatus. In such examples, the apparatus may use the received information directly for determining the correction information and/or the retina, and/or it may further process the received information. For example, the topographic information and/or the distance information of the retina of the eye relative to the anterior surface of the cornea relating to a patient may be retrieved from a memory, a database, a server in a cloud, and/or from corresponding diagnostic devices, or these may simply be input by an operator of the apparatus, e.g., a surgeon.

In an example, the topographic information of the anterior surface and the topographic information of the posterior surface of the lens of the eye may be obtained for near vision and/or for far vision. As described above, topographic information of the lens may include a profile. In some examples, this profile may be obtained for far vision and/or for near vision. This profile may possibly also be obtained for a radius corresponding to a diameter of the pupil of the eye and detected according to a predefined light environment (e.g. for far vision), or an even smaller radius may be considered (e.g. for near vision). In some examples, a radius around the corneal apex (or a center of the anterior corneal surface) may be considered, preferably obtained by a pupillometer. Notably, in case of use of the pupil data detected by a pupillometer, it needs not to be part of the apparatus for that matter, but it would be sufficient if the apparatus is adapted to receive corresponding pupil data, e.g. from a storage device, or from the operator of the apparatus via a corresponding interface. For example, correction information may be individually determined in each of the zones determined by the areas within the radii of the pupil of the eye for near vision and far vision. Thus, the correction information may comprise correction information specific to one or more of the zones for near vision and far vision.

In some examples, the means for determining the correction information may be adapted to perform, based on the topographic information of the anterior surface and of the posterior surface of the cornea and the topographic information of the anterior surface and of the posterior surface of the lens, ray-tracing for at least one light ray passing through the cornea and being refracted by the anterior and posterior surfaces of the cornea and passing through the lens and being refracted by the anterior and posterior surfaces of the lens, such as to optimize focusing on the retina. The same considerations as described with respect to ray-tracing above are also applicable here.

In some examples, the apparatus may further comprise means for obtaining distance information of the posterior surface of the cornea relative to the anterior surface of the cornea of the individual eye and/or a distance of an anterior surface of the lens of the eye relative to the anterior surface of the cornea of the individual eye, and/or a distance of a posterior surface of the lens of the eye relative to the anterior surface of the cornea of the individual eye. The means for determining correction information relating to the anterior surface of the cornea, such as to optimize focusing onto a retina of the eye, may be further adapted to base the determining on the obtained at least one distance information. Using in addition to the topographic information (e.g. a profile) of the corneal surface(s), the lens surface(s), and the refractive indices of the relevant materials (known to the skilled person) also the obtained distance information allows to further refine, e.g., the above outlined ray-tracing. The distance information may also be used in the ray-tracing process outlined in the preceding paragraph.

In an example, the apparatus according to the first and/or second embodiment may be adapted to obtain the topographic information of the anterior corneal surface and the posterior corneal surface of the cornea of the eye from a corneal tomographer. The tomographer may be based on light scattering techniques and/or ultrasonic techniques, etc. Additionally or alternatively, optical coherence tomography techniques may be used.

In a further example, the apparatus may further be adapted to obtain the topographic information of the anterior surface of the lens and the posterior surface of the lens, e.g., obtained from optical coherence tomography techniques or ultrasound techniques.

In a further example, the apparatus may be adapted to obtain the distance information of the posterior surface of the cornea relative to the anterior surface of the cornea of the individual eye and/or a distance of an anterior surface of the lens of the eye relative to the anterior surface of the cornea of the individual eye, and/or a distance of a posterior surface of the lens of the eye relative to the anterior surface of the cornea of the individual eye from a biometer. The biometer may be based on ultrasound techniques or optical coherence tomography techniques.

In a further example, the topographic information of the anterior corneal surface and the posterior corneal surface obtained from the corneal tomographer and the topographic information of the anterior surface of the lens and the posterior surface of the lens from an optical coherence tomographer may be used for ray-tracing, as described herein. For example, the correction that needs to be applied to a certain point on the anterior surface of the cornea (obtained from the corneal tomographer) is determined, such that the light ray passing through that point is optimally focused onto the retina, as calculated based on the (corrected) anterior surface topography and based on the topographic information of the posterior surface (obtained from the corneal tomographer) and the topographic information of the anterior surface of the lens and the posterior surface of the lens (obtained from an optical coherence tomographer). In some examples, this may be done without any fitted parameters. In some examples, only the topographic information of the anterior corneal surface and the posterior corneal surface (obtained from the corneal tomographer) and the topographic information of the anterior surface of the lens and the posterior surface of the lens (obtained from the optical coherence tomographer) may be used. In some examples, also the distance information obtained from a biometer (e.g., an optical biometer) may be used for ray-tracing.

The apparatus may comprise the tomographer. The use of the corneal tomographer allows, e.g., in contrast to corneal topographers based on Placido rings, not only the determination of anterior corneal surface properties but also properties regarding the thickness of the cornea, and in particular the posterior surface. For example, the corneal tomographer may provide topographic information such as a profile of the anterior and the posterior surfaces of the cornea. It may also provide thickness information about the cornea. It may also provide more detailed information about the individual layers of the cornea, such as a corneal epithelium and/or a corneal stroma. In some examples, topographic information regarding the various layers of the cornea may also be taken into account when determining the correction information, as mentioned, which may allow an even more precise determination of the target anterior corneal surface to optimize vision.

In a further example, the apparatus may be adapted to obtain the topographic information, at least in part, from a pupillometer to determine a (photopic) diameter of a pupil of the eye. The apparatus may comprise such a pupillometer. The pupillometer may also be used to define a minimum region of the anterior corneal surface for which the visual ametropia may be corrected, the region having a diameter determined according to a predefined light environment. In some examples, the region may also be determined subjectively and received by the apparatus. Alternatively, the operator may preselect the region of the eye which is to be treated and may then, in a next step, refine the preselected region by using the information provided by the pupillometer, e.g., by using the pupil diameter. All in all, this allows to precisely limit the region of the cornea which is to be treated by the laser procedure. Consequently, the invasiveness of the surgical treatment may be reduced.

In a further example, the apparatus may also comprise means for correcting an aberration of the eye based on the determined correction information, preferably a laser to remove corneal tissue. For example, an excimer laser or a solid-state laser may be used to that end. In other examples, the apparatus may be adapted to determine the correction information such that it may be provided to a laser to remove corneal tissue, without the laser necessarily being part of the apparatus.

In some examples, the apparatus may be adapted to control the means for correcting with a closed-loop feedback. For example, the apparatus may comprise means for controlling a laser (or more generally: the means for correcting) based on updated topographic information of the anterior surface of the cornea. During ablation by the laser, the topographic information of the anterior surface of the cornea may be updated, e.g. in real-time, and the ablation may be controlled accordingly, e.g. in a closed-loop. For example, the ablation may be stopped if a sufficient agreement is reached between the updated topographic information and the correction information, e.g. a target profile of the anterior surface of the cornea, while it may be controlled to continue as long as such agreement has not been reached.

The apparatus may also be adapted to store the determined correction information, e.g., on a memory, in a database, or a server. The correction information may then be retrieved by the means for correcting the aberration of the eye, e.g. the laser, which may be part of the apparatus or which may be separately provided.

In an example, the corneal tomographer, the optical coherence tomographer, the biometer, the scanning laser refractometer and/or the wave-front analyzer, the laser, and optionally the pupillometer may be comprised by the apparatus such that they are an integral part of the apparatus. In such examples, the apparatus may comprise a processing and/or control unit (e.g. a computer) which interacts with the mentioned other parts of the apparatus. For example, the topographic information and/or the refractive aberration information may be transmitted to the processing and/or control unit, e.g. via one or more wires and/or wirelessly. For example, the correction information may similarly be transmitted from the processing and/or control unit to the laser. In another example, the various mentioned parts may not necessarily be an integral part of the apparatus, thereby providing a modular set-up. In this example, the apparatus (which may still comprise a processing unit) may be adapted to exchange the topographic information, the refractive aberration information, and/or correction information, e.g. via one or more wires and/or wirelessly. For example, the respective information may be wirelessly transmitted to and from the apparatus, respectively.

It is noted that the aspects relating to the determining of the desired focusing point relative to the retina may be combined with the further aspects of the present invention, but it may also be implemented independently from these further aspects. For example, a method and/or apparatus may be provided related to obtaining topographic information of an anterior surface and topographic information of a posterior surface of a cornea of an eye. Further, refractive aberration information for the eye may be obtained. A desired focus point may be determined based on the topographic information of the anterior surface and of the posterior surface of the cornea, and based on refractive aberration information, e.g. by ray-tracing.

A further embodiment of the present invention relates to a computer program comprising instructions for carrying out the steps and/or implementing the means described herein. For example, the computer program may be stored on a memory medium and it may cause a processor to implement the individual steps. The memory medium and/or the processor may be comprised by an apparatus according to the present invention. The apparatus of the present invention may generally comprise the computer program of the present invention.

A further embodiment of the present invention relates to a method for visual ametropia correction. The method may comprise the step of obtaining topographic information of an anterior surface and topographic information of a posterior surface of a cornea of an eye. The method may further comprise the step of obtaining a desired focusing point within the eye. The method may further comprise determining correction information relating to the anterior surface of the cornea, such as to optimize focusing onto the desired focusing point, based on the topographic information of the anterior surface and of the posterior surface of the cornea. The method may optionally also comprise further steps, which are described herein with reference to an apparatus and/or a computer program. The method may not include the steps for actually correcting the aberration of the eye based on the determined correction information.

4. BRIEF DESCRIPTION OF THE FIGURES

Figure 2A:
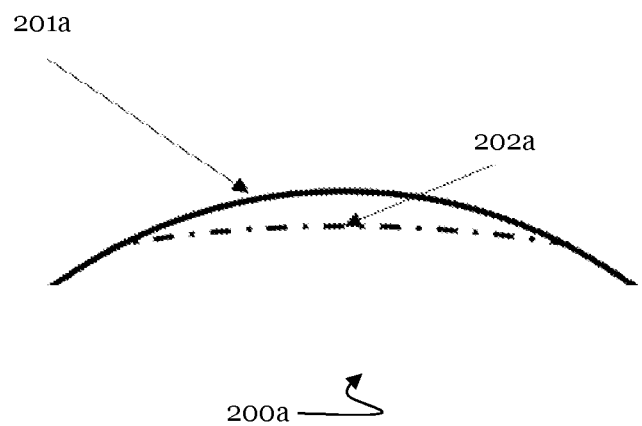
Figure 2B:
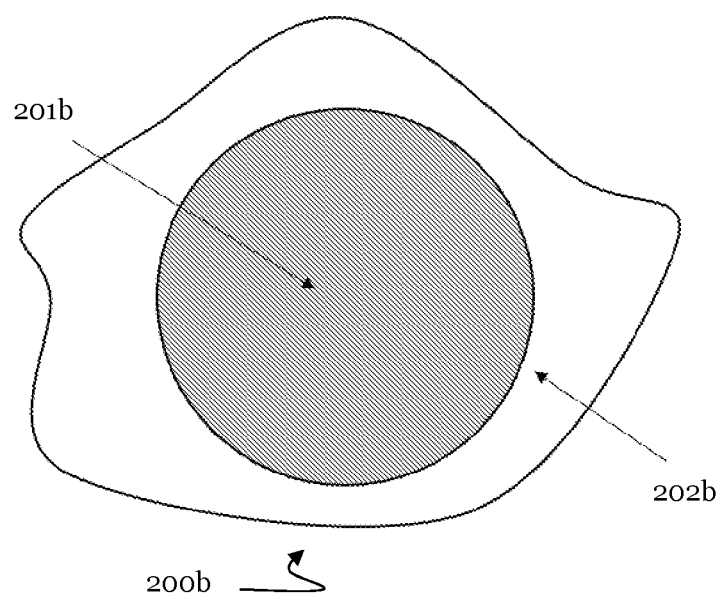

Possible embodiments of the present invention will be described in more detail in the subsequent detailed description with reference to the following Figures:

FIG. 1a/b: Example flow chart for customized corneal ablation according to an example of the present invention;

FIG. 2a: Schematic representation of an exemplary corneal cross-section including an anterior corneal surface of an eye and a target anterior corneal surface;

FIG. 2b: Top view of an example region of an anterior corneal surface which may be surgically treated comprising a monofocal refractive zone and a customized connecting zone.

Figure 2C:
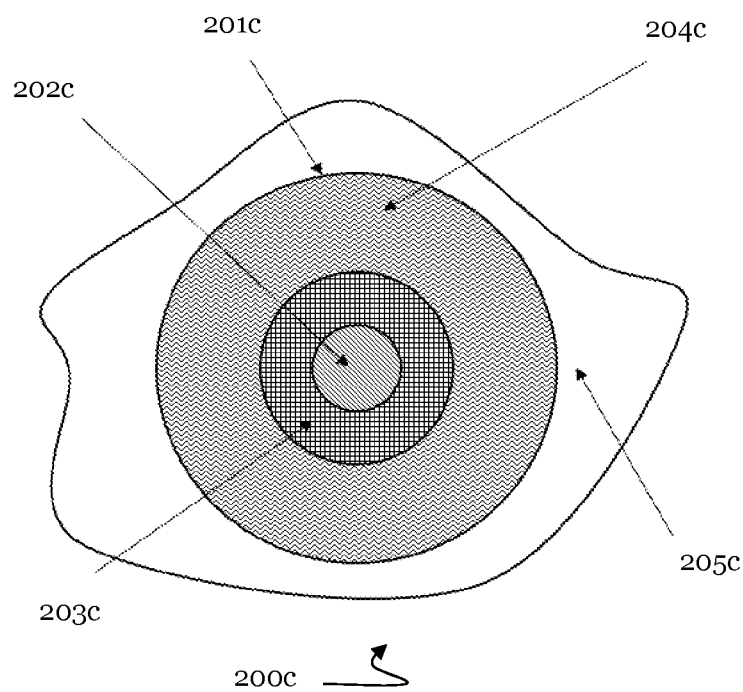

FIG. 2c: Top view of an example region of the cornea which is to be surgically treated comprising a multifocal refractive zone subdivided into a near vision zone, an intermediate vision zone, and a far vision zone, and a customized connecting zone surrounding the multifocal zone.

Figure 3:
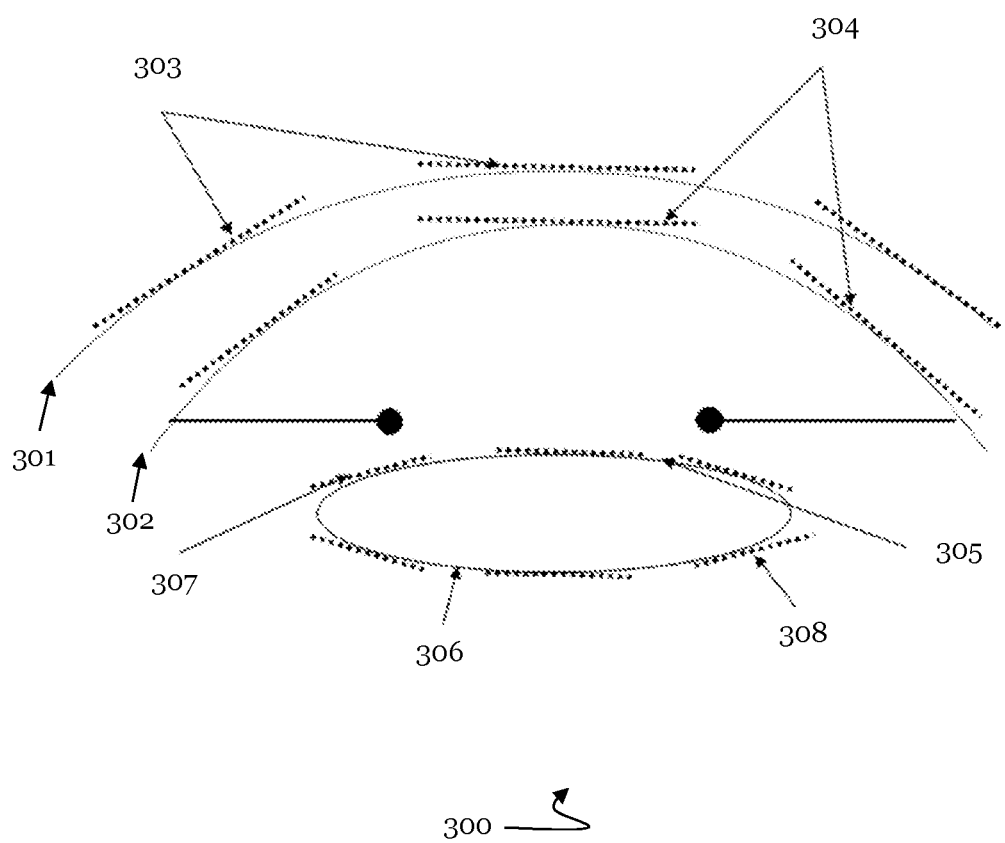

FIG. 3: Schematic representation of an exemplary corneal cross-section with a lens cross-section, wherein the corneal cross-section comprises an anterior corneal surface, a posterior corneal surface, and slopes for various points on the anterior and the posterior corneal surfaces, and the cross-section of the lens comprises anterior and posterior surfaces and slopes for various points on the anterior and posterior surfaces of the lens.

FIG. 4a: Example for determining a region of the anterior surface of the cornea relevant for vision based on the topographic information of the anterior and posterior corneal surfaces and based on a predefined, preferably photopic pupil diameter.

Figure 4B:
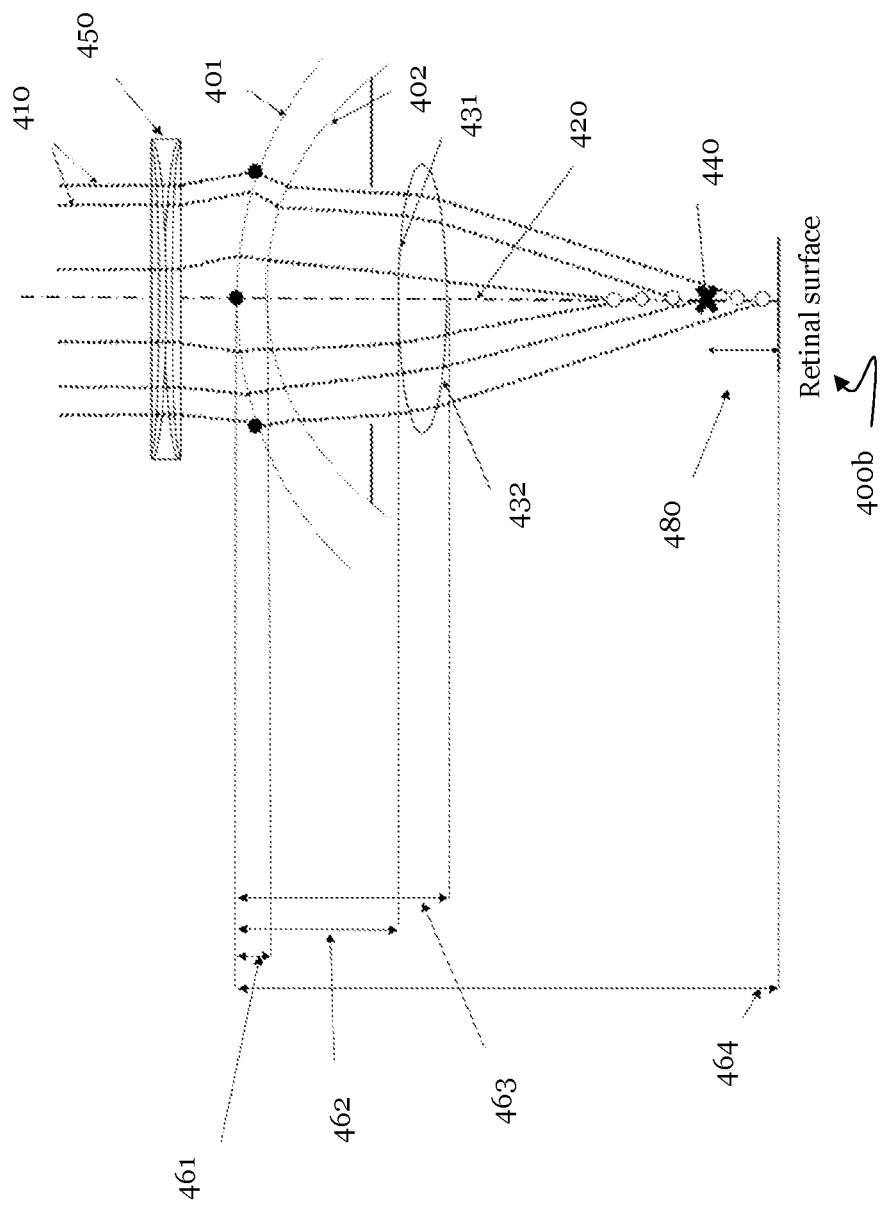

FIG. 4b: Example for determining a desired focusing point based on the topographic information of the anterior and posterior corneal surfaces, topographic information of an anterior and a posterior surface of a lens model estimating the lens of the eye, distance information of the posterior surface of the cornea relative to the anterior surface of the cornea, distance information of the anterior surface of the lens model relative to the anterior surface of the cornea, distance information of the posterior surface of the lens model relative to the anterior surface of the cornea, distance information of the retinal surface relative to the anterior surface of the cornea and based on refractive aberration information.

Figure 4C:
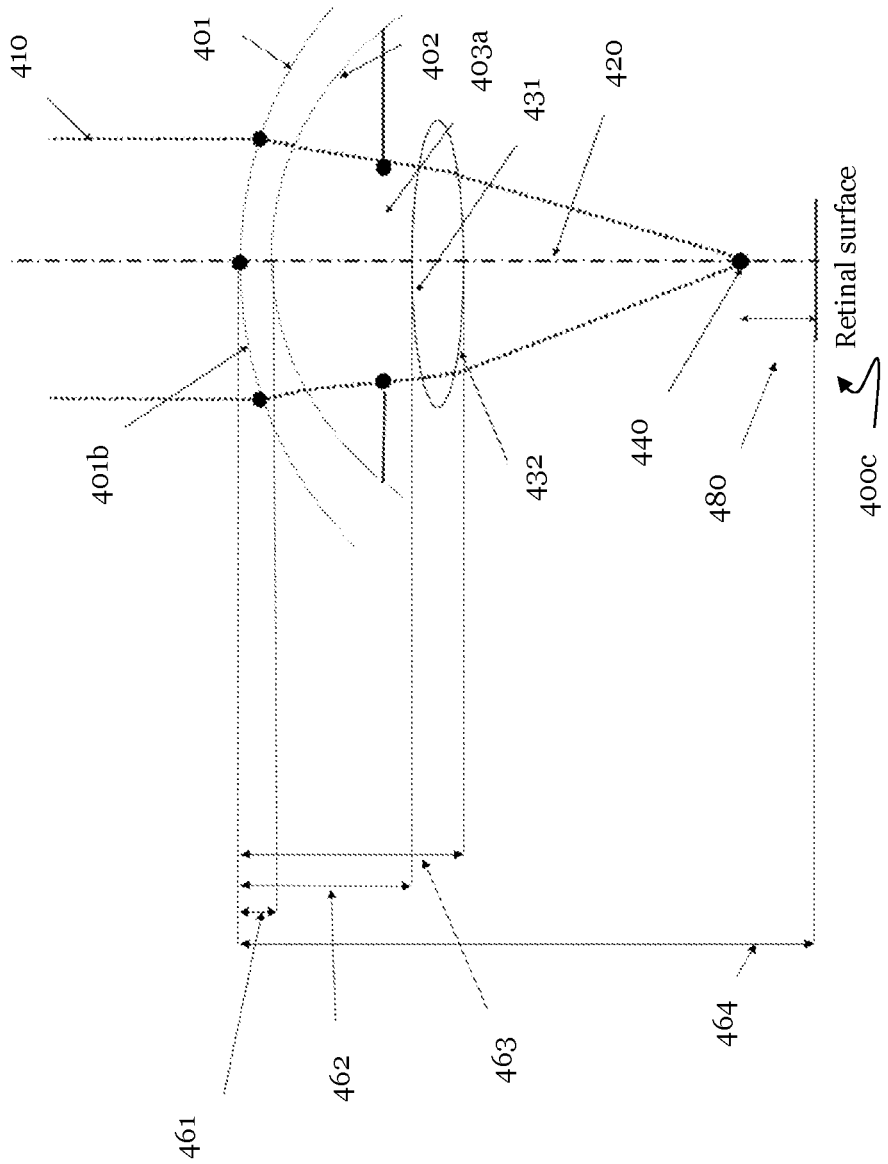

FIG. 4c: Example for determining a region of the anterior surface of the cornea for which correction information is to be calculated based on the topographic information of the anterior and posterior corneal surfaces, topographic information of an anterior and a posterior surface of a lens model estimating the lens of the eye, distance information of the posterior surface of the cornea relative to the anterior surface of the cornea, distance information of the anterior surface of the lens model relative to the anterior surface of the cornea, distance information of the posterior surface of the lens model relative to the anterior surface of the cornea, distance information of the retinal surface relative to the anterior surface of the cornea, based on the desired focusing point and based on the diameter of the pupil of the eye, detected according to a predefined light environment.

Figure 5A:
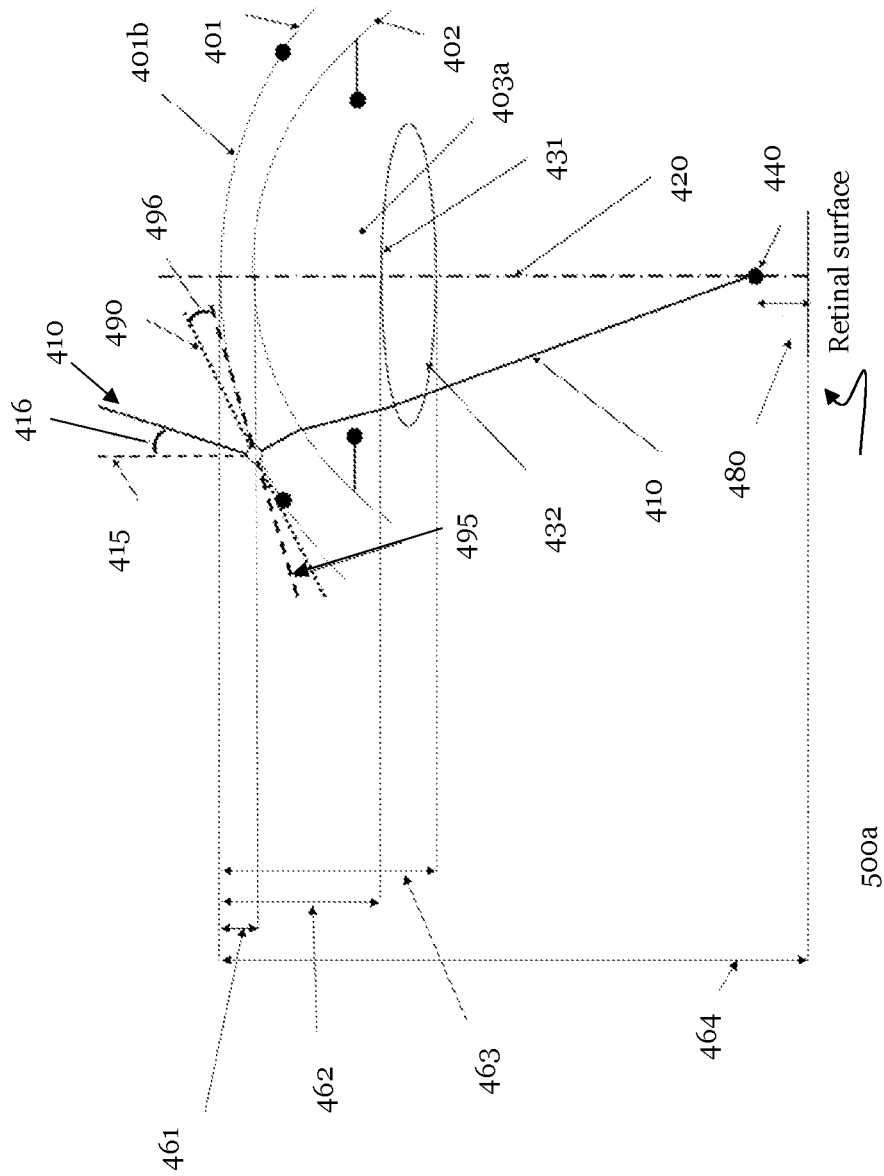

FIG. 5a: First example for determining correction information based on the topographic information of the anterior and posterior corneal surfaces, topographic information of the anterior and posterior surfaces of a lens model estimating the lens of the eye, distance information of the posterior surface of the cornea relative to the anterior surface of the cornea, distance information of the anterior surface of the lens model relative to the anterior surface of the cornea, distance information of the posterior surface of the lens model relative to the anterior surface of the cornea, distance information of the retinal surface relative to the anterior surface of the cornea and based on the desired focusing point by reverse ray-tracing.

Figure 5B:
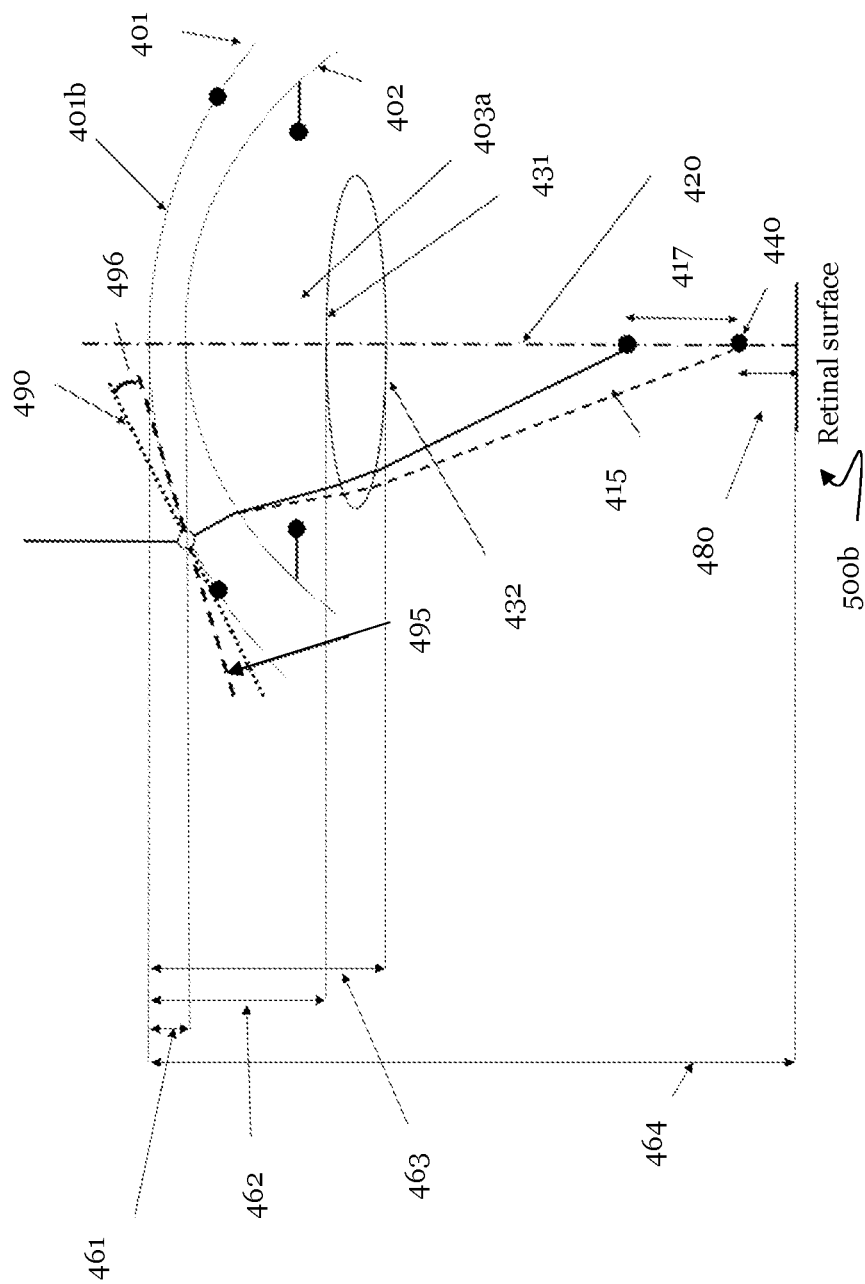

FIG. 5b: Second example for determining correction information based on the topographic information of the anterior and posterior corneal surfaces, topographic information of the anterior and posterior surfaces of a lens model estimating the lens of the eye, distance information of the posterior surface of the cornea relative to the anterior surface of the cornea, distance information of the anterior surface of the lens model relative to the anterior surface of the cornea, distance information of the posterior surface of the lens model relative to the anterior surface of the cornea, distance information of the retinal surface relative to the anterior surface of the cornea and based on the desired focusing point by forward ray-tracing.

Figure 5C:
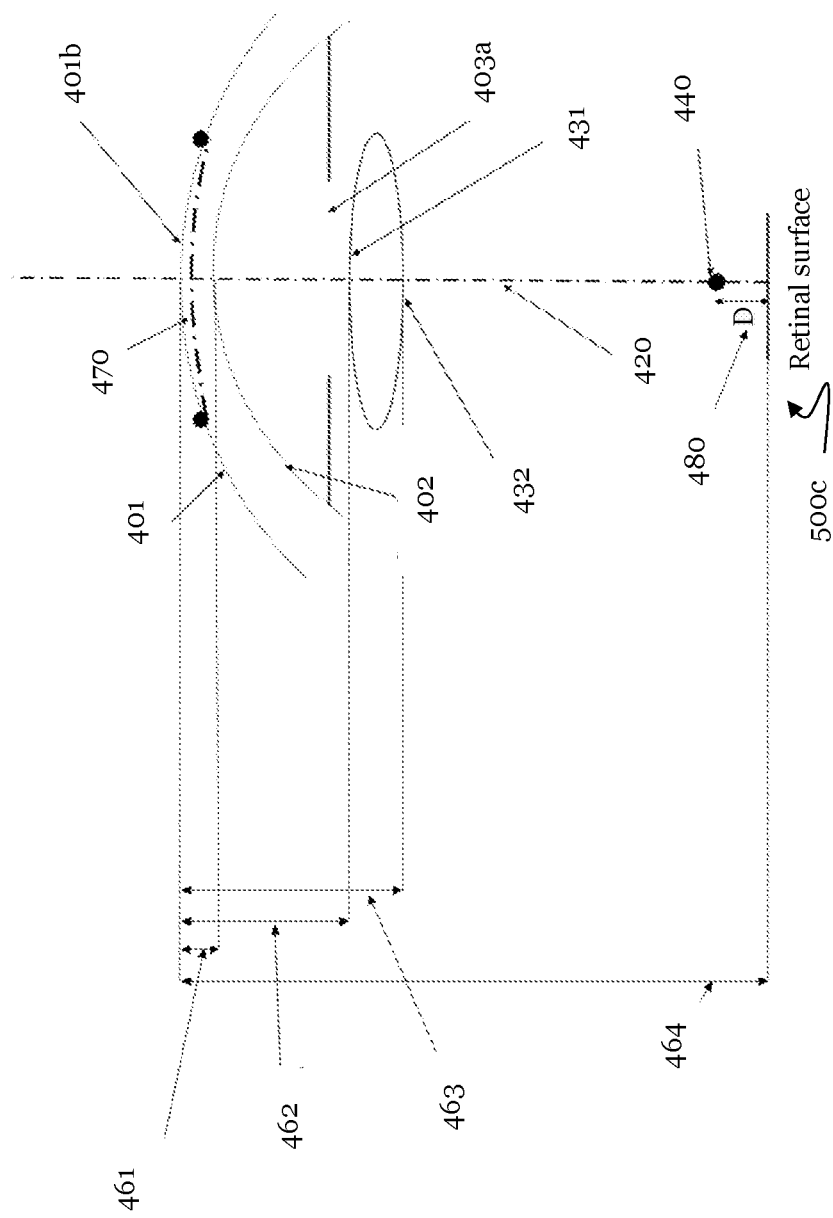

FIG. 5c: Exemplary cross-section of a cornea with a target profile of the anterior corneal surface obtained from the examples according to FIGS. 5a and 5b.

Figure 6A:
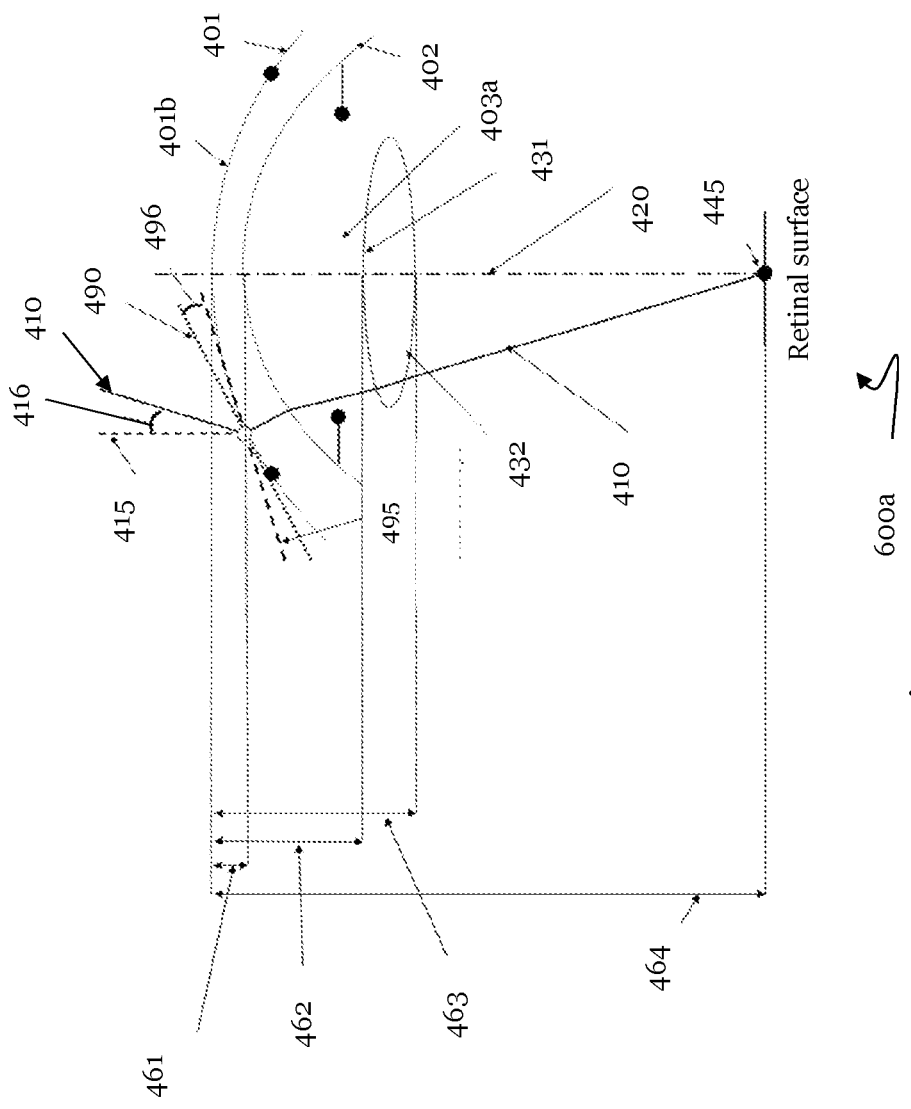

FIG. 6*a*: First example for determining correction information based on the topographic information of the anterior and posterior corneal surfaces, topographic information of the anterior and posterior surfaces of the lens of the eye, distance information of the posterior surface of the cornea relative to the anterior surface of the cornea, distance information of the anterior surface of the lens relative to the anterior surface of the cornea, distance information of the posterior surface of the lens relative to the anterior surface of the cornea, distance information of the retinal surface relative to the anterior surface of the cornea and based on the retina by reverse ray-tracing.

Figure 6B:
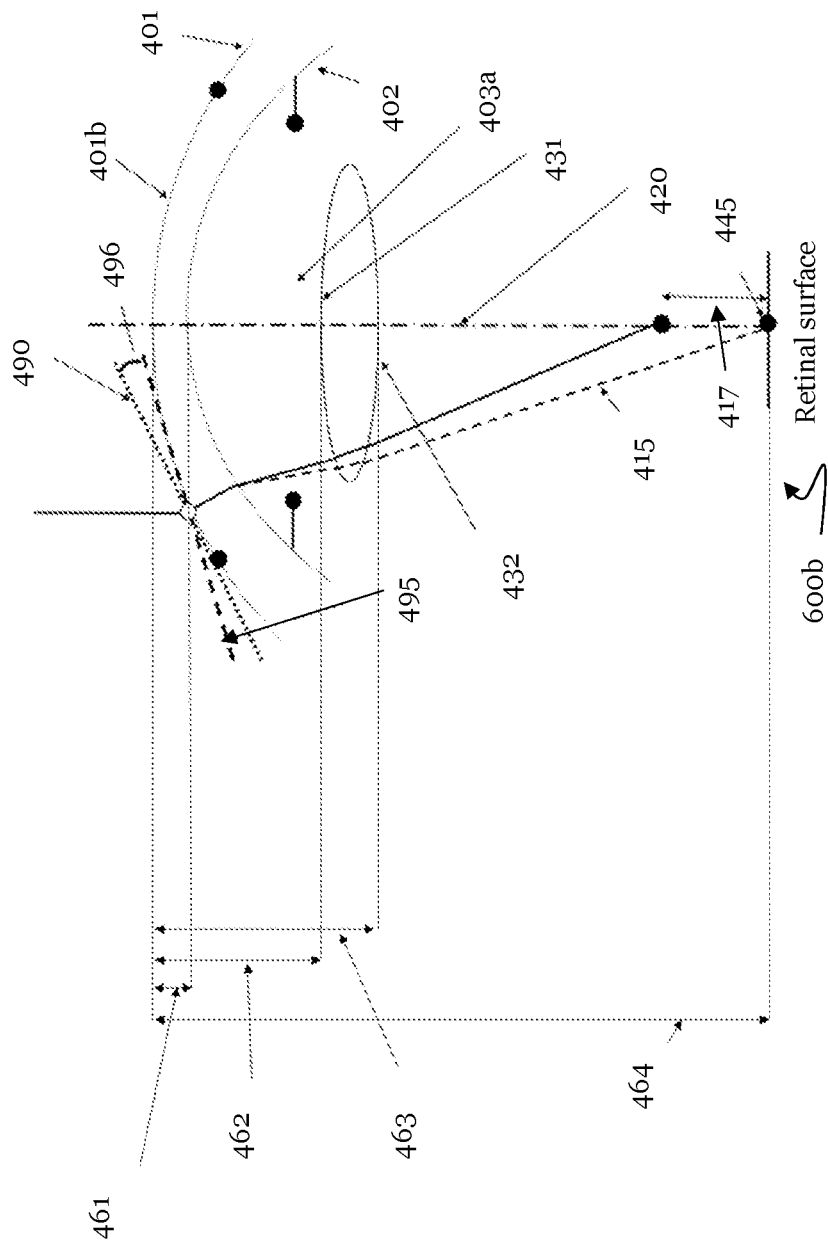

FIG. 6*b*: Second example for determining correction information based on the topographic information of the anterior and posterior corneal surfaces, topographic information of the anterior and posterior surfaces of the lens of the eye, distance information of the posterior surface of the cornea relative to the anterior surface of the cornea, distance information of the anterior surface of the lens relative to the anterior surface of the cornea, distance information of the posterior surface of the lens relative to the anterior surface of the cornea, distance information of the retinal surface relative to the anterior surface of the cornea and based on the retina by forward ray-tracing.

Figure 6C:
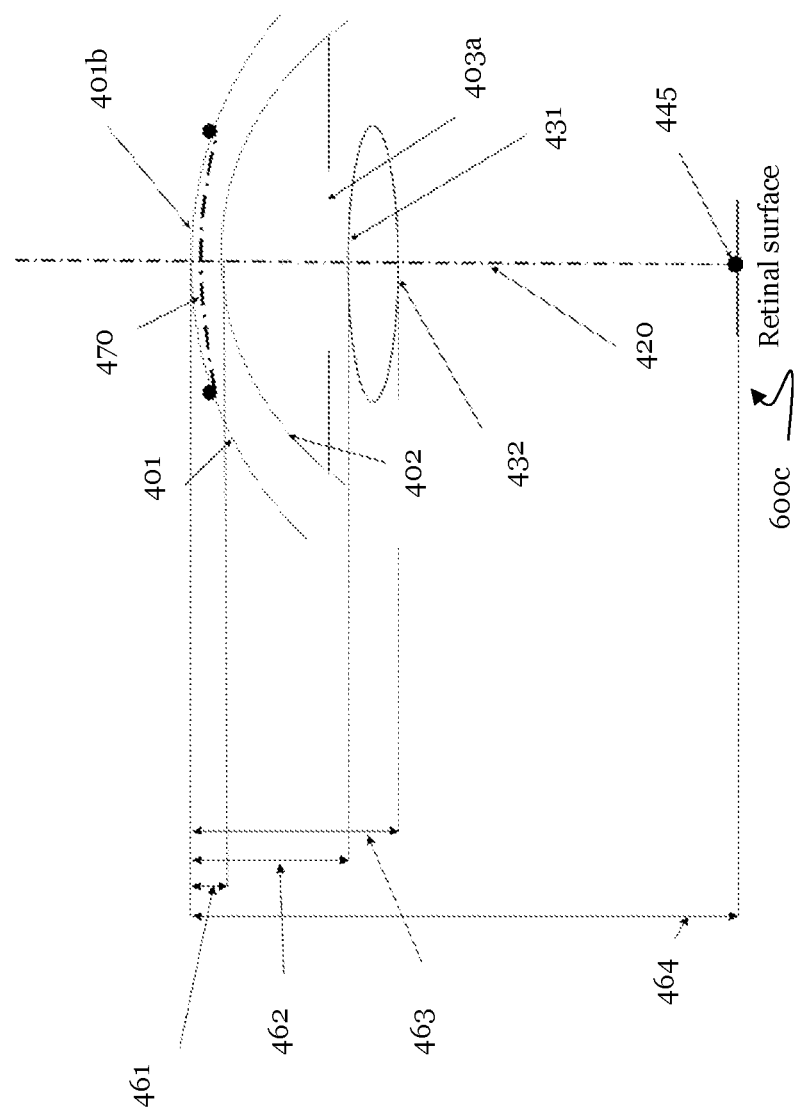

FIG. 6*c*: Exemplary cross-section of a cornea with a target profile of the anterior corneal surface obtained from the example according to FIG. 6*a*.

5. DETAILED DESCRIPTION OF POSSIBLE EMBODIMENTS

Possible embodiments of the present invention will be described in the following. For brevity, only a few embodiments can be described. The skilled person will recognize that the specific features described with reference to these embodiments may be modified and combined differently and that individual features may also be omitted if they are not essential. The general explanations in the sections above will also be valid for the following more detailed explanations.

FIG. 1*a/b* shows an example flow chart 100 for customized corneal ablation by means of an apparatus according to the present invention.

In this example, an apparatus comprises a corneal tomographer 101, a control unit 105 (e.g., a computer, e.g. a central control unit), a biometer 108, and an excimer or solid state laser 106. Reference numeral 102 indicates an operator, e.g., a treating doctor. In this example, the apparatus may optionally comprise a pupillometer 103, and/or a scanning laser refractometer and/or a wave-front analyzer 104 and/or a database 109, and/or an optical coherence tomographer (OCT) and/or the ultrasound scanning system 107.

The corneal tomographer 101 may be adapted to provide topographic information of the anterior corneal surface and the posterior corneal surface. The tomographer may be based on light scattering techniques, ultrasonic techniques, and/or optical coherence tomography, for example. The provided topographic information may comprise a profile, and possibly a slope profile and/or a curvature profile, of the anterior and the posterior surfaces of the cornea. It may also provide thickness information about the cornea and/or even more detailed information about the individual layers of the cornea, such as a corneal epithelium and/or a corneal stroma.

At reference number 102, refractive aberration information for the eye may be obtained by the apparatus from an operator, e.g., the treating doctor. This information may be refractive aberration information, which may, e.g., be subjectively be determined by the operator based on the operator's clinical experience. For example, correction information may include spherical dioptrical correction, cylindrical dioptrical correction and related axis, etc., as may be determined by a usual vision test or by a schiascopic examination or by an autorefractometer.

Additionally or alternatively to the refractive aberration information obtained from the operator, such information may be obtained from a scanning laser refractometer and/or a wave-front analyzer 104. The scanning laser refractometer and/or the wave-front analyzer may provide refractive aberration information such as a refractive error map, e.g., for a cross-section of the cornea, and/or for a two-dimensional region of the surface of the cornea. For example, the refractive error may be expressed as angular errors or angular slopes or any other suitable format. The refractive error may relate to an error as a function of planar x and y (or any other) coordinates of the anterior corneal surface.

The optical corneal tomographer (OCT) and/or the ultrasound scanning system 107 may be adapted to provide topographic information of the anterior surface and the posterior surface of the lens of the eye. As described above with regard to the anterior and posterior corneal surface, the provided topographic information may comprise a profile, and possibly a slope profile and/or a curvature profile, of the anterior and the posterior surfaces of the lens of the eye. It may also provide thickness information about the lens.

The biometer 108 may be adapted to provide distance information of the posterior surface of the cornea relative to the anterior surface of the cornea of the eye and/or a distance information of an anterior surface of the lens of the eye relative to the anterior surface of the cornea of the eye, and/or a distance information of a posterior surface of the lens of the eye relative to the anterior surface of the cornea of the eye, and/or distance information about the retina of the eye relative to the anterior surface of the cornea of the eye. The biometer may be based on ultrasound biometry or optical biometry (e.g., using partial coherence interferometry). The distance information may be e.g., expressed as a function of planar x and y (or any other) coordinates of the anterior corneal surface.

The pupillometer 103 may be used to determine, e.g., the photopic pupil diameter, e.g. the pupil diameter detected according to a set of predefined light environments, eventually associated with a statistical probability of said light environment occurring. The photopic pupil diameter may be preferably but not mandatorily used to define the desired focusing point and the pupil diameter detected according to a set of predefined light environments, eventually associated with a statistical probability of said light environment occurring, may be preferably but not mandatorily used to limit the region of the cornea which is to be surgically treated. The regions of the cornea corresponding to the photopic pupil diameter and to the pupil diameter detected according to a set of predefined light environments, eventually associated with a statistical probability of said light environment occurring, are determined by means of a ray tracing process. This may allow, e.g., the operator to better refine the preselected region of the cornea for treatment. Moreover, it may be determined which region of the cornea should be used for determining a desired focusing point (e.g., by means of ray-tracing). For the above determinations, it may be useful, if the iris plane is determined such that the projection of the pupil diameter onto the anterior surface may be calculated more precisely (i.e., individually for the patient's eye geometry). To this end, the apparatus and/or the corneal tomographer may include means for determining the iris plane and/or means for obtaining such information. Alternatively, such corneal regions may be arbitrarily selected by the operator.

The database 109 may be used, e.g., to model the lens of the individual eye. The database 109 may comprise profiles, and possibly slope profiles and/or curvature profiles of a number of anterior and posterior surfaces of different lenses. The lens information may relate to data measured from different individuals and/or they may relate to generic models. Also, thickness information and/or distance information relative to the anterior corneal surface of the different lenses may be available in the database. Alternatively, the lens model may arbitrarily be selected by the operator.

The control unit 105 may be adapted to obtain information regarding an optical axis of the eye. The optical axis may be determined by the control unit 105, e.g. based on information provided by the tomographer or predefined by the operator. It may also be determined by the tomographer 101 and obtained by the control unit 105 from the tomographer 101. It may, however, also be determined by other means, and input to the control unit 105, e.g. by the operator. The optical axis may, e.g., be selected as an (approximate) symmetry axis of the cornea.

Similarly, the control unit 105 may be adapted to obtain information regarding a center of vision of the cornea, at which the optical axis may be centered. This may correspond to a corneal apex. The center of vision may be determined by the control unit 105, e.g. based on information provided by the tomographer or predefined by the operator. It may also be determined by the tomographer 101, e.g., based on the corneal apex or based on a light fixation reflex on the anterior corneal surface or based on the symmetry axis of the cornea, and obtained by the control unit 105 from the tomographer 101. It may, however, also be determined by other means, and input to the control unit 105, e.g. by the operator.

The topographic information obtained, e.g., from the corneal tomographer 101, the optical coherence tomographer (OCT) and/or the ultrasound scanning system 107, and/or from the database 109, and/or the distance information from the biometer 108, and/or possibly the pupillary information collected from the pupillometer 103, and/or the refractive aberration information obtained, e.g., from the operator 102 and possibly by the scanning laser refractometer and/or by the wave-front analyzer 104, may be obtained by the control unit 105 of the apparatus. The control unit 105 may then determine based on the obtained information a correction information. The control unit may be adapted to determine the correction information as generally described in the above section "Summary of the Invention", and as further described with respect to FIGS. 2-6 below. In some examples, also further properties of the individual patient's eye may be taken into account in the determination of the correction information, e.g. topographic information regarding the retina and/or the fovea relative to the cornea. The correction information may for example be expressed in terms of a customized ablation volume of corneal tissue. For example, the correction information may relate to an ablation depth, e.g., expressed in micrometers as a function of planar x and y (or any other) coordinates of the anterior corneal surface. The topographic information of the anterior and posterior corneal surfaces may relate to similar coordinates. Further exemplary details on the determination of the correction information will be provided with reference to FIGS. 4a-4c, 5a-5c, and FIG. 6a-6b. The control unit 105 may further be adapted to mutually control and coordinate the further elements of the apparatus.

The determined correction information may then be provided, e.g., to the excimer or solid-state laser 106, which may ablate the corneal tissue by using, e.g., a sequence of deliberately set of "laser shots". The laser 106 may comprise a coupling interface for reading the correction information from the control unit 105. After performing one or more "laser shots", at least in part based on the correction information, the resulting anterior corneal shape may be inspected, e.g., by means of a topographic (or morphological) and/or dioptrical inspection. In an example, the corneal tomographer 101 may provide updated topographic information of the anterior corneal surface after ablation. In another example, the scanning laser refractometer and/or the wave-front analyzer 104 may additionally or alternatively provide updated refractive aberration information after ablation. This updated topographic information and/or refractive aberration information may then be used to determine whether the target anterior corneal surface has been obtained. If, after the entire ablation has been performed, the desired anterior surface or refractive error elimination has not been achieved, the control unit 105 may determine a further volume for corneal tissue ablation, which may then be removed by the excimer or solid-state laser 106. Instead of applying such feedback after the entire ablation has been performed, it may also be applied in real-time, or after ablating certain portions of the entire planned ablation, for example, such that possible calibration errors of the laser may be taken into account. If the target profile of the anterior corneal surface is obtained, then the procedure for customized ablation may be stopped.

In an example, the control unit 105 may represent an embodiment of an apparatus of the present invention. In other examples, the corneal tomographer 101 and/or the optical coherence tomographer (OCT) and/or the ultrasound scanning system 107 and/or the biometer 108 and/or the laser 106 may or may not be part of the apparatus. The control unit 105 may possibly be adapted to have an interface to the corneal tomographer 101 and/or the optical coherence tomographer (OCT) and/or the ultrasound scanning system 107 and/or the biometer 108 and/or the laser 106. It may allow to receive data from the corneal tomographer 101 and/or the optical coherence tomographer (OCT) and/or the ultrasound scanning system 107 and/or the biometer 108 and/or the laser 106 and/or to control laser 106.

In some examples, the control unit 105 may optionally be coupled permanently (e.g., in a wired or wireless manner) to any of the corneal tomographer 101 and/or the optical coherence tomographer (OCT) and/or the ultrasound scanning system 107 and/or the biometer 108 and/or the laser 106. However, this is not necessary. In other examples, the control unit 105, the corneal tomographer 101 and/or the optical coherence tomographer (OCT) and/or the ultrasound scanning system 107 and/or the biometer 108 and/or the laser 106 may exchange data (unidirectionally in each direction and/or bidirectionally) via a temporal coupling or via a data carrier (e.g., a USB device moved from one device to the other, a server to which they have common access, and/or any other available data carrier).

FIG. 2a shows a schematic representation of a corneal cross-section 200a. The schematic representation depicts topographic information, i.e. a profile 201a, of the anterior corneal surface, e.g., measured by using a corneal tomographer. Further, a target profile 202a of the anterior corneal surface is depicted. The volume delimited by the actual profile 201a and the target profile 202a of the anterior corneal surface defines the volume of the corneal tissue which may be ablated, e.g., by an excimer or a solid-state laser, i.e. the target ablation volume.

FIG. 2b shows a schematic representation of a top view of a region of cornea 200b which may be analyzed and/or treated. The region comprises a monofocal zone 201b. The monofocal zone 201b may define the region of the cornea which may be treated such that the quality of vision is optimized for far distances. In an example, the monofocal zone may be determined by the treating doctor and/or by the pupillometer 103 explained with reference to FIG. 1a/b, e.g. selected to correspond to a projection of the pupil diameter detected according to a set of predefined light environments, eventually associated with a statistical probability of said light environment occurring. The monofocal zone 201b may additionally be surrounded by a customized connecting zone 202b. The customized connecting zone 202b connects the treated zone, i.e., the monofocal zone 201b in this example, with an untreated area of the anterior corneal surface. A perimeter of the customized connecting zone 202b may be arbitrarily chosen such that the perimeter comprises an irregular shape. The customized connecting zone 202b may be used and its perimeter may be chosen such as to minimize a risk of regression, haze, and starburst effects, and it may further facilitate healing of the cornea after treatment.

FIG. 2c shows a further schematic representation of a top view of a region of a cornea 200c. The region of the cornea comprises a multifocal zone 201c, and a customized connecting zone 205c surrounding the multifocal zone 201c. Similarly as explained with regard to FIG. 2b, the customized connecting zone 205c may connect the perimeter of the treated zone, i.e., the multifocal zone 201c in this example, with the untreated area of the anterior corneal surface. The multifocal zone 201c may be further sub-divided into a near vision zone 202c, an intermediate vision zone 203c, and a far vision zone 204c. As explained with reference to the example in FIG. 2b, the multifocal zone 201c as well as the sub-zones of the multifocal zone 201c may be determined by the treating doctor and/or by the pupillometer 103 of FIG. 1a/b. Further, the operator may determine a different refractive correction and/or different refractive error maps for the sub-zones of the multifocal zone 201c, such that a different refractive aberration information and/or a different desired focusing point may be used in each of the zones. The refractive aberration information may comprise refractive aberration information specific to one or more of the near vision zone 202c, the intermediate vision zone 203c, and the far vision zone 204c. Similarly, the focusing point may differ for these zones. The corresponding correction information for each zone, may then be determined based thereon, as generally outlined herein, e.g. by considering only the regions of the anterior and corresponding posterior corneal surfaces as well as the anterior and corresponding posterior surfaces of the lens falling within the respective zones. Thus, the near vision zone 202c for vision in a near field, the intermediate vision zone 203c for vision in an intermediate field, and the far vision zone 204c for vision in a far field may be optimized individually. In other words, the correction information may comprise correction information specific to one or more of the near vision zone 202c, the intermediate vision zone 203c, and the far vision zone 204c.

FIG. 3 shows another schematic representation of a corneal cross-section 300. The cross-section 300 shows topographic information, i.e. a profile 301, of the anterior corneal surface and topographic information, i.e. a profile 302, of the posterior corneal surface. It further shows topographic information, i.e. a profile, of the anterior surface of the lens of the eye and topographic information, i.e. a profile, of the posterior surface of the lens of the eye. The profiles of both the anterior and the posterior corneal surfaces may be obtained, e.g., by the corneal tomographer 101 explained with reference to FIG. 1a/b. The profiles of both the anterior and the posterior surfaces of the lens of the eye may be obtained, e.g., by the optical coherence tomographer (OCT) and/or the ultrasound scanning system 107 or they may be obtained from the database 109 explained with reference to FIG. 1a/b. Further, FIG. 3 depicts slopes 303 and 304 at various points on the anterior corneal surface 301 and, respectively, the posterior corneal surface 302. Additionally, slopes 307 and 308 at various points on the anterior surface of the lens 305 and, respectively, the posterior surface of the lens 306. The slopes 303, 304 and the slopes 307, 308 are relevant for the refractive behavior of the cornea and the refractive behavior of the lens (e.g., to calculate angles of refraction as determined by Snell's law), and they may also be determined by the corneal tomographer 101 and, respectively, the optical coherence tomographer and/or the ultrasound scanning system 107 or they may be obtained from the database 109 or derived from information provided by the corneal tomographer 101 and, respectively, the optical coherence tomographer (OCT) and/or the ultrasound scanning system 107, e.g., by calculating the respective tangent. As discussed in more detail below, the slopes 303 of the anterior corneal surface may be modified by means of laser ablation such that a target profile of the anterior corneal surface 301 may be obtained which optimizes vision in view of the refraction provided by the slopes 304 of the posterior corneal surface 302 and the slopes 307 and 308 of the anterior 305 and the posterior 306 surfaces of the lens.

FIG. 4a shows another schematic representation of a corneal cross-section 400. Cross-section 400 comprises topographic information, i.e., a profile 401, of the anterior corneal surface and topographic information, i.e., a profile 402, of the posterior corneal surface. Moreover, the schematic comprises an iris plane 404, wherein the iris defines a pupil 403. Pupil 403 may correspond to a photopic pupil. An optical axis 420 may be defined, e.g., based on the visual axis of the eye, e.g. being an axis of symmetry of the cornea, e.g. selected by the operator. Moreover, a center 405 of the anterior corneal surface may defined, e.g., as the corneal apex or the light fixation reflex on the anterior corneal surface or based on the symmetry axis of the cornea or selected by the operator.

Optionally, a region of the anterior corneal surface 401a may be determined, which corresponds to a projection of the photopic pupil (i.e., assuming rays impinging onto the cornea in a manner parallel to the optical axis). Hence, that region of the anterior corneal surface 401a that is relevant to determine the desired focusing point (light rays impinging on other regions of the cornea will be blocked by the iris) may be determined. Based on the topographic information of both the anterior and posterior surfaces of the cornea, and based on the generally known refractive indices of the cornea and the aqueous humour within the cornea, the rays may be traced by calculating the respective refraction angles, e.g., based on Snell's law.

FIG. 4b shows an example for determining a desired focusing point based on topographic information for the anterior surface 401 of the cornea, based on topographic information for the posterior surface 402 of the cornea, based on topographic information for the anterior surface 431 of the lens (e.g., a lens model estimating the lens of the eye as obtained from the database 109 as explained with respect to FIG. 1a/b), based on topographic information for the posterior surface 432 of the lens (e.g., a lens model estimating the lens of the eye as obtained from the database 109 as explained with respect to FIG. 1a/b) and based on refractive aberration information. In this example, light rays 410 are propagating towards the cornea in a manner parallel to the optical axis 420. The light rays are refracted by optical means 450, e.g. mimicking a lens, that corresponds to a correction of the refractive aberration information. For example, if the refractive aberration information corresponds to a subjective refraction with a spherical and a cylindrical aberration with a relative axis, the optical means 450 could be a lens adapted to correct that spherical and cylindrical aberration. In case of more complex refractive aberration information, e.g. involving higher order aberrations, the optical means 450 may be defined accordingly, e.g., mimicking a more complex lens.

The light rays 410 refracted by the optical means 450 subsequently impinge on the anterior corneal surface 401, propagate through the cornea and impinge on the posterior corneal surface 402, wherein the posterior corneal surface is at a distance from the anterior corneal surface as indicated by the distance 461 at the optical axis 420, which may correspond to the corneal apex (wherein the distance information may be obtained by the biometer 108 and/or the tomographer 101 as explained with respect to FIG. 1a/b). The light rays then propagate through the anterior chamber and impinge on the anterior surface 431 of the lens (e.g., a lens model as obtained from the database 109 as explained with respect to FIG. 1a/b). Subsequently, the light rays further propagate through the lens and impinge on the posterior surface 432 of the lens (e.g., a lens model as obtained from the database 109 as explained with respect to FIG. 1a/b), which may be located at distances 462 and 463 relative to the anterior corneal surface 401 measured at the optical axis 420 (e.g., obtained by the biometer 108 as explained with respect to FIG. 1a/b). Based on the topographic information of the anterior and posterior corneal surfaces 401, 402 and the anterior and posterior surfaces 431, 432 of the lens (e.g., a lens model as obtained from the database 109 as explained with respect to FIG. 1a/b), the refraction at these various surfaces may be calculated and the rays may be traced such that their intersections with the optical axis 420 within the eye may be determined. Here, the calculation may be limited to rays impinging on a region of the anterior corneal surface 401, e.g., region 401a determined as outlined with respect to FIG. 4a. Alternatively, the calculation may be limited to any of regions 202c, 203c or 204c as outlined with reference to FIG. 2c, e.g. if near-vision, intermediate vision or far-vision is to be analyzed separately.

From the intersections, a desired focusing point 440 may be determined. For example, a weighted average of all intersections may be used. In the simplest case, a center-of-mass calculation may be used, or a calculation with varying weight factors may be used, e.g. giving more weight to central rays. A decreasing weight may be given to the determined intersections according to the radial distance between the center of vision and the respective impinging light ray on the anterior corneal surface.

It is noted that in other examples, the focusing point may be defined differently, e.g. based on the refractive aberration the operator would like to correct, based on the position of the fovea or retina of the patient's eye, or arbitrarily by the operator. The corresponding determination may be performed by the operator or a separate device, in which case the apparatus according to the present invention has a corresponding interface to obtain the desired focusing point 440. However, the corresponding determination may also be performed by the apparatus itself.

From the determined desired focusing point 440, a distance to the retina 480, which may be at a distance 464 (at the optical axis 420) relative to the anterior corneal surface (obtained, e.g., by the biometer 108 as explained with respect to FIG. 1a/b), may be determined. This distance 480, which defines a position of the desired focusing point 440 relative to the retina, may serve as reliability measure, e.g., for the lens model as obtained from the database 109 and/or the refractive aberration information provided by the operator 102 and/or obtained by the scanning refractometer and/or wavefront analyzer 104. For example, if the distance 480 is above a threshold, e.g., above 500 µm, more preferably above 300 µm, most preferably above 100 µm, a warning may be issued, e.g., an audio signal, indicating the operator, e.g., the treating doctor, that the available data may be erroneous. The operator may then re-evaluate the obtained information.

Additionally or alternatively, determining the desired focusing point 440 may also be based on reverse ray-tracing. The determinations based on forward ray-tracing and reverse ray-tracing may be applied alternatively or in addition to each other, e.g. alternatingly in one or more iterations, or separately from each other, wherein a weighted average (or a simple average) of the respectively determined desired focusing point may then be determined.

FIG. 4c shows a further step that may be implemented, in which a region 401b of the anterior corneal surface is determined, to which the subsequent calculation of the correction information and/or treatment may be limited. The region 401b may be determined based on the desired focusing point 440 and on a selected pupil diameter 403a, for example a pupil diameter detected according to a set of predefined light environments, eventually associated with a statistical probability of said light environment occurring or a pupil diameter by which the patient's actual pupil diameter during daily life is expected to be limited with a certain likelihood. For example, a diameter may be selected such that 80%-100%, preferably about 95%, of all situations during the patient's daily life comprise a pupil diameter that does not exceed the selected diameter.

The apparatus shown in FIG. 1a/b, specifically control unit 105, may be adapted to perform any of the steps outlined with reference to FIGS. 4a-4c.

FIG. 5a shows a first example for determining correction information by reverse ray-tracing. In this example, the determination is based on a light ray 410 emerging from the desired focusing point 440, which is at a distance 480 relative to the retina. To each point or portion (e.g. of a grid, as outlined earlier) on a selected region 401b of the anterior corneal surface 401 and each corresponding point on the posterior corneal surface 402, the anterior surface 431 of the lens (e.g., a lens model as obtained from the database 109 as explained with respect to FIG. 1a/b), and the posterior surface 432 of the lens (e.g., a lens model as obtained from the database 109 as explained with respect to FIG. 1a/b), a light ray may be traced. Similarly as described with respect to FIG. 4b, the posterior surface of the lens, the anterior surface of the lens, and the posterior corneal surface may be located a distances 461, 462, and respectively, 463 relative to the anterior corneal surface, and exemplary indicated for the optical axis 420 (wherein these distances may be obtained by the biometer 108 as described with respect to FIG. 1a/b). For each point, a correction information may be determined in the form of an angle 416 between the light ray 410, as exiting the cornea, and the direction 415 of the optical axis 420. An angle deviation between the light ray 410 as exiting from the cornea and the direction of the optical axis 420 indicates ametropia. The determination may include determining a refraction of the light ray 410 when impinging on the posterior surface 432 of the lens (e.g., a lens model as obtained from the database 109 as explained with respect to FIG. 1a/b), determining a refraction of the light ray 410 when impinging on the anterior surface 431 of the lens (after having propagated through the lens, e.g., a lens model as obtained from the database 109 as explained with respect to FIG. 1a/b), and determining a refraction of the light ray 410 when impinging on the posterior corneal surface 402 (which may be included in or determined from the topographic information of the posterior surface 402, e.g. a profile of the posterior surface). Similarly, it includes determining a refraction of the light ray 410 impinging on the anterior corneal surface 401 (after having propagated through the cornea) having a local slope 490.

A local target slope 495 of the anterior surface 401 may then be determined such that the light beam 410 impinging on an anterior surface having such slope 495 would be refracted such that it exits the cornea in the direction 415 of the optical axis 420. Additionally or alternatively, an angle 496 between the local slope 490 and the local target slope 495 of the anterior surface 401 may be calculated. In that manner, the local target slopes 495 may be determined for each portion or point within region 401b. For example, by integrating the local target slopes 495, correction information in the form of a desired target profile 470 (see FIG. 5c below) of the region 401b of the anterior surface 401 may be determined.

Optionally, the desired target profile 470 of the corneal anterior surface 401 within region 401b is then translated along the optical axis 420 such that a smooth transition between the target profile within region 401b and the anterior surface 401 outside region 401b may be obtained if desired. In this step, it is also ensured that all points of the target profile are located within the actual profile of the anterior corneal surface 401.

The above steps outlined with reference to FIG. 5a may then be re-iterated one or more times, wherein the topographic information of the anterior surface is replaced by the target profile of the anterior surface obtained from the respective previous iteration. Such iteration may yield a more and more refined target profile, which optimizes focusing to the desired focusing point 440. Possibly, modifications to the angles 496 are applied in each iteration to optimize focusing onto the desired focusing point 440. By iterating the process, focusing optimization onto the desired focusing point 440 may be achieved.

Additionally or alternatively to the translating of the desired target profile 470 (see FIG. 5c below) of the corneal anterior surface 401 within region 401b along the optical axis 420 in between the iterations, such translation may be performed as a final step, i.e., after completing the iteration(s).

From an intersection between the topographic information of the anterior surface 401 and the target profile of the anterior corneal surface 202a defined as the determined target profile 470, possibly inclusive of the connecting zone 202b, an ablation volume may be determined. Correction information may thus also be provided in the form of an ablation volume.

Particularly in the calculation outlined with respect to FIG. 5a, it is beneficial to take into account topographic information regarding the posterior corneal surface as well as the lens model. Local irregularities of the posterior shape of the cornea may strongly influence the refraction at each point as well as the correction needed at each point. Taking these into account leads to an improved vision correction optimized for the individual patient and may minimize the ablation volume.

FIG. 5b shows a further example for determining correction information, which is similar to that shown in FIG. 5a. However, instead of using rays emerging from the desired focusing point 440, as outlined with reference to FIG. 5a, rays 410 are used that impinge on the selected region 401b of the cornea in a manner parallel to the optical axis 420, i.e. forward ray-tracing is used. Similarly, as outlined with reference to FIG. 5a, based on local slopes 490 of the anterior corneal surface 401, of the posterior corneal surface 402, of the anterior surface of the lens model 431 and of the posterior surface of the lens model 432 respectively, each ray 410 may be traced until it intersects the optical axis 420 within the eye. For each ray, a position deviation 417 of that intersection from the desired focusing point 440 may be determined.

A local target slope 495 of the anterior surface 401 may be determined such that the light beam 410 is focused onto the desired focusing point 440 (or a deviation therefrom is minimized). Additionally or alternatively, an angle 496 between the local slope 490 and the local target slope 495 of the anterior surface may be determined. In that manner, the local target slopes 495 may be determined for each portion or point within a selected region 401b. For example, by integrating the local target slopes 495, a desired target profile of the anterior surface 401 may be determined, as outlined above with reference to FIG. 5a. Moreover, also the iterations and/or translation(s) along the optical axis 420 may be performed similarly also for the example outlined with reference to FIG. 5b.

Similarly as explained with reference to FIG. 5a, it is especially beneficial to take into account topographic information regarding the posterior corneal surface 402, the anterior and posterior surfaces 431, 432 of the lens model, and the individual distance information 461, 462, 463, 464 also for the determinations of FIG. 5b.

The determinations outlined with reference to FIGS. 5a and 5b may be applied alternatively or in addition to each other, e.g. alternatingly in one or more iterations, or separately from each other, wherein a weighted average (or a simple average) of the respectively determined correction information may then be determined. The regions 401b may be selected as any of the regions outlined herein.

The apparatus shown in FIG. 1a/b, specifically control unit 105, may be adapted to perform any of the steps outlined with reference to FIGS. 5a-5b.

FIG. 5c shows a further exemplary cross-section, in which exemplary correction information on the form of target profile 470 of the anterior corneal surface is shown, as determined as outlined with reference to FIGS. 5a-5b.

FIG. 6a shows another example for determining correction information by reverse ray-tracing. In this example, the determination is based on a light ray 410 emerging from the retinal surface 445. To each point or portion (e.g. of a grid, as outlined earlier) on a selected region 401b of the anterior corneal surface 401 and each corresponding point on the posterior corneal surface 402, the anterior surface 431 of the lens (e.g. obtained by the OCT and/or the ultrasound scanning system 107 as explained with respect to FIG. 1a/b), and the posterior surface 432 of the lens (e.g. obtained by the OCT and/or the ultrasound scanning system 107 as explained with respect to FIG. 1a/b), a light ray may be traced. Similarly as described with respect to FIG. 4b, the posterior surface of the lens, the anterior surface of the lens, and the posterior corneal surface may be located a distances 461, 462, and respectively, 463 relative to the anterior corneal surface, and exemplary indicated for the optical axis 420 (wherein these distances may be obtained by the biometer 108 as described with respect to FIG. 1*a/b*). For each point, a correction information may be determined in the form of an angle 416 between the light ray 410, as exiting the cornea, and the direction 415 of the optical axis 420. An angle deviation between the light ray 410 as exiting from the cornea and the direction of the optical axis 420 indicates ametropia. The determination may include determining a refraction of the light ray 410 when impinging on the posterior surface 432 of the lens (e.g. obtained by the OCT and/or the ultrasound scanning system 107 as explained with respect to FIG. 1*a/b*), determining a refraction of the light ray 410 when impinging on the anterior surface 431 of the lens (after having propagated through the lens, e.g., obtained by the OCT and/or the ultrasound scanning system 107 as explained with respect to FIG. 1*a/b*), and determining a refraction of the light ray 410 when impinging on the posterior corneal surface 402 (which may be included in or determined from the topographic information of the posterior surface 402, e.g. a profile of the posterior surface). Similarly, it includes determining a refraction of the light ray 410 impinging on the anterior corneal surface 401 (after having propagated through the cornea) having a local slope 490.

A local target slope 495 of the anterior surface 401 may then be determined such that the light beam 410 impinging on an anterior surface having such slope 495 would be refracted such that it exits the cornea in the direction 415 of the optical axis 420. Additionally or alternatively, an angle 496 between the local slope 490 and the local target slope 495 of the anterior surface 401 may be calculated. In that manner, the local target slopes 495 may be determined for each portion or point within region 401*b*. For example, by integrating the local target slopes 495, correction information in the form of a desired target profile 470 (see FIG. 6*c* below) of the region 401*b* of the anterior surface 401 may be determined.

Optionally, the desired target profile 470 of the corneal anterior surface 401 within region 401*b* is then translated along the optical axis 420 such that a smooth transition between the target profile within region 401*b* and the anterior surface 401 outside region 401*b* may be obtained if desired. In this step, it is also ensured that all points of the target profile are located within the actual profile of the anterior corneal surface 401.

The above steps outlined with reference to FIG. 6*a* may then be re-iterated one or more times, wherein the topographic information of the anterior surface is replaced by the target profile of the anterior surface obtained from the respective previous iteration. Such iteration may yield a more and more refined target profile, which optimizes focusing to the retinal surface 445. Possibly, modifications to the angles 496 are applied in each iteration to optimize focusing onto the retinal surface 445. By iterating the process, focusing optimization onto the retinal surface 445 may be achieved.

Additionally or alternatively to the translating of the desired target profile 470 (see FIG. 6*c* below) of the corneal anterior surface 401 within region 401*b* along the optical axis 420 in between the iterations, such translation may be performed as a final step, i.e., after completing the iteration(s).

From an intersection between the topographic information of the anterior surface 401 and the target profile of the anterior corneal surface 202*a* defined as the determined target profile 470, possibly inclusive of the connecting zone 202*b*, an ablation volume may be determined. Correction information may thus also be provided in the form of an ablation volume.

Particularly in the calculation outlined with respect to FIG. 6*a*, it is beneficial to take into account topographic information regarding the posterior corneal surface as well as the anterior and posterior surfaces of the lens. Local irregularities of the posterior shape of the cornea may strongly influence the refraction at each point as well as the correction needed at each point. Taking these into account leads to an improved vision correction optimized for the individual patient and may minimize the ablation volume.

FIG. 6*b* shows a further example for determining correction information, which is similar to that shown in FIG. 6*a*. However, instead of using rays emerging from the retinal surface 445, as outlined with reference to FIG. 6*a*, rays 410 are used that impinge on the selected region 401*b* of the cornea in a manner parallel to the optical axis 420, i.e. forward ray-tracing is used. Similarly, as outlined with reference to FIG. 6*a*, based on local slopes 490 of the anterior corneal surface 401, of the posterior corneal surface 402, of the anterior surface of the lens 431 and of the posterior surface of the lens 432 respectively, each ray 410 may be traced until it intersects the optical axis 420 within the eye. For each ray, a position deviation 417 of that intersection from the retinal surface 445 may be determined.

A local target slope 495 of the anterior surface 401 may be determined such that the light beam 410 is focused onto the retinal surface 445 (or a deviation therefrom is minimized). Additionally or alternatively, an angle 496 between the local slope 490 and the local target slope 495 of the anterior surface may be determined. In that manner, the local target slopes 495 may be determined for each portion or point within a selected region 401*b*. For example, by integrating the local target slopes 495, a desired target profile of the anterior surface 401 may be determined, as outlined above with reference to FIG. 6*a*. Moreover, also the iterations and/or translation(s) along the optical axis 420 may be performed similarly as outlined with reference to FIG. 6*a*.

Similarly as explained with reference to FIG. 6*a*, it is especially beneficial to take into account topographic information regarding the posterior corneal surface 402, the anterior and posterior surfaces 431, 432 of the lens, and the individual distance information 461, 462, 463, 464 also for the determinations of FIG. 6*b*.

The determinations outlined with reference to FIGS. 6*a* and 6*b* may be applied alternatively or in addition to each other, e.g. alternatingly in one or more iterations, or separately from each other, wherein a weighted average (or a simple average) of the respectively determined correction information may then be determined. The regions 401*b* may be selected as any of the regions outlined herein.

The apparatus shown in FIG. 1*a/b*, specifically control unit 105, may be adapted to perform any of the steps outlined with reference to FIGS. 6*a*-6*b*.

FIG. 6*c* shows a further exemplary cross-section, in which exemplary correction information on the form of target profile 470 of the anterior corneal surface is shown, as determined as outlined with reference to FIGS. 6*a*-6*b*.

Additionally or alternatively, the obtained topographic information about the anterior and posterior corneal surface 401, 402, the topographic information about the anterior and posterior surface 433, 434 of the lens, and possible also the various distance information 461, 462, 463, 464 as described with respect to FIG. 6a may be used to determine a desired focusing point 440 similarly as described with respect to FIG. 4a to 4c. Similarly as described above, a distance 480 of the determined desired focusing point relative to the retina may be determined. If this distance is above a second threshold, e.g., above 500 μm, more preferably above 300 μm, most preferably above 100 μm, a warning may be issued, similarly as described above.

The invention claimed is:

1. An apparatus for visual ametropia correction, comprising:
   a. electronic device means for obtaining topographic information of an anterior surface and topographic information of a posterior surface of a cornea of an individual eye;
   b. electronic device means for obtaining measured distance information of a retina of the eye relative to the anterior surface of the cornea of the individual eye;
   c. electronic device means for determining a position of a desired focusing point relative to the retina, based on the topographic information of the anterior surface and of the posterior surface of the cornea, and refractive aberration information for the eye;
   wherein it is verified whether the desired focusing point is indeed located on or in proximity to the retina based on the measured distance information, and the apparatus verifies a reliability of the topographic information and/or the measured distance information based on the position of the desired focusing point relative to the retina.

2. The apparatus according to claim 1, further comprising means for obtaining distance information of at least one of: an anterior surface of a lens of the eye and a posterior surface of the lens relative to the anterior surface of the cornea of the individual eye, and positioning a lens model estimating the lens of the eye.

3. The apparatus according to claim 2, wherein the means for determining the position of the desired focusing point relative to the retina is further adapted to base the determining on a lens model estimating the lens of the eye.

4. The apparatus according to claim 1, wherein the apparatus is adapted to issue a warning if the position of the desired focusing point relative to the retina exceeds a predetermined threshold.

5. The apparatus according to claim 1, wherein the means for obtaining the desired focusing point is further adapted to determine the desired focusing point by ray tracing of at least one light ray refracted according to the topographic information of the anterior surface and of the posterior surface of the cornea, and according to optical means that correspond to a correction of the refractive aberration information for the eye.

6. The apparatus according to claim 1, further comprising means for determining correction information relating to the anterior surface of the cornea to optimize focusing onto the desired focusing point, based on the topographic information of the anterior surface, of the posterior surface of the cornea.

7. An apparatus for visual ametropia correction, comprising:
   a. electronic device means for obtaining measured topographic information of an anterior surface and measured topographic information of a posterior surface of a cornea of an individual eye;
   b. electronic device means for obtaining measured topographic information of an anterior surface and measured topographic information of a posterior surface of a lens of the individual eye;
   c. electronic device means for obtaining distance information of a retina of the eye relative to the anterior surface of the cornea of the individual eye;
   d. electronic device means for determining correction information relating to the anterior surface of the cornea to optimize focusing onto the retina of the eye, based on the measured topographic information of the anterior surface and of the posterior surface of the cornea and the measured topographic information of the anterior surface and of the posterior surface of the lens.

8. The apparatus according to claim 7, wherein the measured topographic information of the anterior surface and the measured topographic information of the posterior surface of the lens of the eye is obtained for near vision and/or for far vision.

9. The apparatus according to claim 7, wherein the means for determining the correction information is adapted to perform, based on the measured topographic information of the anterior surface and of the posterior surface of the cornea and the measured topographic information of the anterior surface and of the posterior surface of the lens, ray-tracing for at least one light ray passing through the cornea and being refracted by the anterior and posterior surfaces of the cornea and passing through the lens and being refracted by the anterior and posterior surfaces of the lens to optimize focusing on the retina.

10. The apparatus according to claim 7, further comprising
    means for obtaining distance information of at least one of: the posterior surface of the cornea, the anterior surface of the lens, the posterior surface of the lens, relative to the anterior surface of the cornea of the individual eye; and
    wherein the means for determining correction information relating to the anterior surface of the cornea to optimize focusing onto a retina of the eye, is further adapted to base the determining on the obtained at least one distance information.

11. A computer program stored on a non-transitory computer-readable storage medium for visual ametropia correction comprising instructions which when executed cause an apparatus to:
    a. obtain topographic information of an anterior surface and topographic information of a posterior surface of a cornea of an individual eye;
    b. obtain measured distance information of a retina of the eye relative to the anterior surface of the cornea of the individual eye;
    c. determine a position of a desired focusing point relative to the retina, based on the topographic information of the anterior surface and of the posterior surface of the cornea, and refractive aberration information for the eye; and
    d. verify whether the desired focusing point is indeed located on or in proximity to the retina based on measured distance information, and verify a reliability of the topographic information and/or the distance information based on the position of the desired focusing point relative to the retina.

12. A computer program stored on a non-transitory computer readable storage medium for visual ametropia correction comprising instructions which when executed cause an apparatus to:

a. obtain measured topographic information of an anterior surface and measured topographic information of a posterior surface of a cornea of an individual eye;
b. obtain measured topographic information of an anterior surface and measured topographic information of a posterior surface of a lens of the individual eye;
c. obtain distance information of a retina of the eye relative to the anterior surface of the cornea of the individual eye; and
d. determine correction information relating to the anterior surface of the cornea to optimize focusing onto the retina of the eye, based on the measured topographic information of the anterior surface and of the posterior surface of the cornea and the measured topographic information of the anterior surface and of the posterior surface of the lens.

13. A method for visual ametropia correction comprising the steps of:
a. obtaining topographic information of an anterior surface and topographic information of a posterior surface of a cornea of an individual eye;
b. obtaining measured distance information of a retina of the eye relative to the anterior surface of the cornea of the individual eye;
c. determining a position of a desired focusing point relative to the retina, based on the topographic information of the anterior surface and of the posterior surface of the cornea, and refractive aberration information for the eye; and
d. verifying whether the desired focusing point is indeed located on or in proximity to the retina based on measured distance information, and verifying a reliability of the topographic information and/or the distance information based on the position of the desired focusing point relative to the retina.

14. A method for visual ametropia correction comprising the steps of:
a. obtaining measured topographic information of an anterior surface and measured topographic information of a posterior surface of a cornea of an individual eye;
b. obtaining measured topographic information of an anterior surface and measured topographic information of a posterior surface of a lens of the individual eye;
c. obtaining distance information of a retina of the eye relative to the anterior surface of the cornea of the individual eye; and
d. determining correction information relating to the anterior surface of the cornea to optimize focusing onto the retina of the eye, based on the measured topographic information of the anterior surface and of the posterior surface of the cornea and the measured topographic information of the anterior surface and of the posterior surface of the lens.

* * * * *